US011963984B2

(12) United States Patent
Bensoussan et al.

(10) Patent No.: US 11,963,984 B2
(45) Date of Patent: Apr. 23, 2024

(54) MESENCHYMAL STEM CELLS OBTAINED FROM WHARTON'S JELLY FOR THE TREATMENT OF SEPSIS

(71) Applicants: UNIVERSITÉ DE LORRAINE, Nancy (FR); CENTRE HOSPITALIER RÉGIONAL UNIVERSITAIRE DE NANCY, Nancy (FR)

(72) Inventors: Danièle Bensoussan, Nancy (FR); Sébastien Gibot, Réméréville (FR); Loïc Reppel, Nancy (FR); Caroline Laroye, Nancy (FR); Amir Boufenzer, Villers-lès-Nancy (FR); Léonore Avercenc, Nancy (FR); Céline Huselstein, Bainville-sur-Madon (FR)

(73) Assignees: UNIVERSITÉ DE LORRAINE, Nancy (FR); CENTRE HOSPITALIER RÉGIONAL UNIVERSITAIRE DE NANCY, Nancy (FR)

(*) Notice: Subject to any disclaimer, the term of this patent is extended or adjusted under 35 U.S.C. 154(b) by 328 days.

(21) Appl. No.: 16/488,253

(22) PCT Filed: Feb. 28, 2018

(86) PCT No.: PCT/FR2018/050472
§ 371 (c)(1),
(2) Date: Aug. 23, 2019

(87) PCT Pub. No.: WO2018/158542
PCT Pub. Date: Sep. 7, 2018

(65) Prior Publication Data
US 2020/0000856 A1 Jan. 2, 2020

(30) Foreign Application Priority Data
Feb. 28, 2017 (FR) ...................... 1751649

(51) Int. Cl.
A61K 35/51 (2015.01)

(52) U.S. Cl.
CPC .................... A61K 35/51 (2013.01)

(58) Field of Classification Search
CPC .... A61K 35/51; A61K 35/28; A61K 38/2013; A61K 38/2086; C12N 5/0668; C12N 5/0605
See application file for complete search history.

(56) References Cited

U.S. PATENT DOCUMENTS

2017/0296588 A1* 10/2017 Ichim ..................... A61K 35/28

FOREIGN PATENT DOCUMENTS

CA 2878299 A1 * 12/2015 ........... C12N 5/0068
CN 103352026 B 8/2016
(Continued)

OTHER PUBLICATIONS

Kim DW, Staples M, Shinozuka K, Pantcheva P, Kang SD, Borlongan CV. Wharton's jelly-derived mesenchymal stem cells: phenotypic characterization and optimizing their therapeutic potential for clinical applications. Int J Mol Sci. 2013;14(6):11692-11712. Published May 31, 2013. (Year: 2013).*
(Continued)

Primary Examiner — Marcia S Noble
Assistant Examiner — Lauren K Van Buren
(74) Attorney, Agent, or Firm — Maier & Maier, PLLC

(57) ABSTRACT

The disclosure relates to human mesenchymal stem cells from Wharton's jelly, a method for preparing them, and the therapeutic uses thereof, in particular for the treatment of sepsis and specifically septic shock. The treatment may involve the administration to a subject in need thereof a pharmaceutical composition including the human mesenchymal stem cells from Wharton's jelly and a pharmaceutically acceptable excipient.

17 Claims, 12 Drawing Sheets

(56) References Cited

FOREIGN PATENT DOCUMENTS

| RU | 2 604 672 C1 | 12/2016 |
|---|---|---|
| WO | 2010/015929 A2 | 2/2010 |
| WO | 2011/101834 A1 | 8/2011 |
| WO | 2011/153205 A1 | 12/2011 |
| WO | 2016/001846 A1 | 1/2016 |

OTHER PUBLICATIONS

Curley GF, Jerkic M, Dixon S, et al. Cryopreserved, Xeno-Free Human Umbilical Cord Mesenchymal Stromal Cells Reduce Lung Injury Severity and Bacterial Burden in Rodent *Escherichia coli*-Induced Acute Respiratory Distress Syndrome. Critical Care Medicine. Feb. 1, 2017;45(2):e202-e212. (Year: 2017).*

Sarugaser R, Ennis J, Stanford WL, et al. Isolation, propagation, and characterization of human umbilical cord perivascular cells (HUCPVCs). Methods Mol Biol 2009;482:269-279. (Year: 2009).*

Ho et al. "The Immunomodulatory and Therapeutic Effects of Mesenchymal Stromal Cells for Acute Lung Injury and Sepsis" Journal of Cellular Physiology 230: 2606-2617, 2015 (Year: 2015).*

Singer et al. "The Third International Consensus Definitions for Sepsis and Septic Shock (Sepsis-3)" JAMA, 2016, 315(8): 801-810 (Year: 2016).*

Francisca Alcayaga-Miranda, et al., "Combination therapy of menstrual derived mesenchymal stem cells and antibiotics ameliorates survival in sepsis", Stem Cell Res Ther., 2015, vol. 6, No. 199, 13 pgs.

Chiara Capelli et al., "Minimally manipulated whole human umbilical cord is a rich source of clinical-grade human mesenchymal stromal cells expanded in human platelet lysate", Cytotherapy, 2011, vol. 13, No. 7, pp. 786-801 (16 pgs.).

Yu-Hua Chao et al., "An increase in CD3+CD4+CD25+ Regulatory T Cells after Administration of Umbilical Cord-Derived Mesenchymal Stem Cells during sepsis", PLoS One, Oct. 2014, vol. 9, No. 10, pp. 1-8 (8 pgs.).

Raghavan Chinnadurai et al., "Cryopreserved MSCs are Susceptible to T-cell Mediated Apoptosis which is Partly Rescued by IFNγ Licensing", Stem Cells, 2016, vol. 34, No. 9, pp. 2429-2442 (20 pgs.).

José M. Cóndor et al., "Treatment With Human Wharton's Jelly-Derived Mesenchymal Stem Cells Attenuates Sepsis-Induced Kidney Injury, Liver Injury, and Endothelial Dysfunction", Stem Cells Transl Med, 2016, vol. 5, No. 8, pp. 1048-1057 (10 pgs.).

James Devaney et al., "Human mesenchymal stromal cells decrease the severity of acute lung injury induced by *E. coli* in the rat", Thorax, 2015, vol. 70, No. 7, pp. 625-635 (11 pgs.). Thorax Online First, published on May 18, 2015 as 10.1136/thoraxjnl-2015-206813.

F. Di Giuseppe et al., "Cryopreservation Effects on Wharton's Jelly Stem Cells Proteome", Stem Cell Rev and Rep, 2014, vol. 10, pp. 429-446 (18 pgs.).

Viktor Y. Dombrovskiy et al., "Rapid increase in hospitalization and mortality rates for severe sepsis in the United States: A Trend Analysis from 1993 to 2003", Crit Care Med, 2007, vol. 35, No. 5, pp. 1244-1250 (42 pgs.).

Moira François et al., "Cryopreserved mesenchymal stromal cells display impaired immunosuppressive properties as a result of heat-shock response and impaired interferon-γ licensing", Cytotherapy, 2012, vol. 14, No. 2, pp. 147-152 (6 pgs.).

Elena Gonzalez-Rey et al., "Human adult stem cells derived from adipose tissue protect against experimental colitis and sepsis", Gut Online First, Jan. 9, 2009, vol. 58, No. 7, pp. 929-939 (30 pgs.). Downloaded from gut.bmj.com on Jul. 3, 2014—published by group.bmj.com. Gut Online First, published on Jan. 9, 2009 as 10.1136/gut.2008.168534.

Oliver W. Gramlich et al., "Cryopreserved Mesenchymal Stromal Cells Maintain Potency in a Retinal Ischemia/Reperfusion Injury Model: Toward an off-the-shelf therapy", Scientific Reports (www.nature.com/scientificreports), 2016, 6:26463, DOI: 10.1038/srep 26463, 12 pgs.

Sean R. R. Hall et al., "Mesenchymal Stromal Cells Improve Survival During Sepsis in the Absence of Heme Oxygenase-1: The Importance of Neutrophils", Stem Cells Translational and Clinical Research, 2013, vol. 31, No. 2, pp. 397-407 (11 pgs.).

Kendra N. Iskander et al., "Sepsis: Multiple Abnormalities, Heterogeneous Responses, and Evolving Understanding", Physiol Rev, 2013, vol. 93, No. 3, pp. 1247-1288 (42 pgs.).

Christian L. Johnson et al., "Concise Review: Mesenchymal Stromal Cell-Based Approaches for the Treatment of Acute Respiratory Distress and Sepsis Syndromes", Stem Cells Translational Medicine (www.StemCellsTM.com), 2017, vol. 6, No. 4, 11 pgs. Stem Cells Translational Medicine published by Wiley Periodicals, Inc. on behalf of AlphaMed Press.

Hani Kim et al., "Mesenchymal stromal (stem) cells suppress pro-inflammatory cytokine production but fail to improve survival in experimental staphylococcal toxic shock syndrome", BMC Immunology, 2014, vol. 15, No. 1, 9 pgs.

Anna Krasnodembskaya et al., "Antibacterial Effect of Human Mesenchymal Stem Cells is Mediated in Part from Secretion of the Antimicrobial Peptide LL-37", Stem Cells Translational and Clinical Research, 2010, vol. 28, No. 12, pp. 2229-2238 (10 pgs.).

Cong-juan Luo et al., "Mesenchymal Stem Cells Ameliorate Sepsis-Associated Acute Kidney Injury in Mice", Shock, 2014, vol. 41, No. 2, pp. 123-129 (7 pgs.).

Paulo S. Martins et al., "Expression of cell surface receptors and oxidative metabolism modulation in the clinical continuum of sepsis", Critical Care, 2008, vol. 12, No. 1, R25, pp. 1-10 (10 pgs.). http://ccforum.com/content/12/1/R25.

Shirley H. J. Mei et al., "Prevention of LPS-Induced Acute Lung Injury in Mice by Mesenchymal Stem Cells Overexpressing Angiopoietin 1", PLoS Medicine, Sep. 2007, vol. 4, No. 9, e269, pp. 1525-1537 (13 pgs.). www.plosmedicine.org.

É. Mezey, et al., "Mesenchymal stem cells and infectious diseases: Smarter than drugs", Immunology Letters, 2015, vol. 68, No. 2, pp. 208-214 (7 pgs.). http:/ddx.doi.org/10.1016/j.imlet.2015.05.020.

Guido Moll et al., "Cryopreserved or Fresh Mesenchymal Stromal Cells: Only a Matter of Taste or Key to Unleash the Full Clinical Potential of MSC therapy?", Advances in Experimental Medicine and Biology, 2016, 951, pp. 77-98 (22 pgs.).

Krisztián Németh et al., "Bone marrow stromal cells attenuate sepsis via prostaglandin E2-dependent reprogramming of host macrophages to increase their interleukin-10 production", Nature Medicine, Jan. 2009, vol. 15, No. 1, pp. 42-49 (9 pgs.).

Irene Oliver-Vila et al., "Evaluation of a cell-banking strategy for the production of clinical grade mesenchymal stromal cells from Wharton's jelly", Cytotherapy, 2015, vol. 18, No. 1, pp. 25-35 (11 pgs.).

Leonardo Pedrazza et al., "Mesenchymal stem cells decrease splenocytes apoptosis in a sepsis experimental model", Inflammation Research, 2014, vol. 63, No. 9, pp. 719-728 (10 pgs.).

Phuc Van Pham et al., "Good manufacturing practice-compliant isolation and culture of human umbilical cord blood-derived mesenchymal stem cells", Journal of Translational Medicine, 2014, vol. 12, No. 56, 10 pgs.

Loïc Reppel, "Potentialité des Cellules Stromales de la Gelée de Wharton en Ingénierie du Cartilage", 2014, Doctoral thesis. Retrieved from http://docnum.univ-lorraine.fr/public/DDOC_T_2014_0164_REPPEL.pdf. 201 pgs.

Mauricio Rojas et al., "Human adult bone marrow-derived stem cells decrease severity of lipopolysaccharide-induced acute respiratory distress syndrome in sheep", Stem Cell Research and Therapy, 2014, vol. 5, No. 42, 12 pgs.

Sharath Belame Shivakumar et al., "Cryopreservation of Human Wharton's Jelly-derived Mesenchymal Stem Cells Following Controlled Rate Freezing Protocol Using Different Cryoprotectants; A Comparative Study", International Journal of Stem Cells, 2015, vol. 8, No. 2, pp. 155-169 (15 pgs.).

Mervyn Singer, MD, et al., "The Third International Consensus Definitions for Sepsis and Septic Shock (Sepsis-3)", JAMA, 2016, vol. 315, No. 8, pp. 801-810 (10 pgs.).

(56) References Cited

OTHER PUBLICATIONS

Christian Unger et al., "Good manufacturing practice and clinical-grade human embryonic stem cell lines", Human Molecular Genetics, 2008, vol. 17, Review Issue 1, pp. R48-53 (6 pgs.).
Kang-Hsi Wu et al., "Time-Series Expression of Toll-Like Receptor 4 Signaling in Septic Mice Treated With Mesenchymal Stem Cells", Shock, 2016, vol. 45, No. 6, pp. 634-640 (7 pgs.).
Xiaoyin Zhao et al., "The Toll-like Receptor 3 Ligand, Poly(I:C), Improves Immunosuppressive Function and Therapeutic Effect of Mesenchymal Stem Cells on Sepsis via Inhibiting MiR-143", Stem Cells, 2014, vol. 32, No. 2, pp. 521-533 (13 pgs.).

\* cited by examiner

MESENCHYMAL STEM CELLS OBTAINED FROM WHARTON'S JELLY FOR THE TREATMENT OF SEPSIS

FIELD

The invention relates to human mesenchymal stem cells from Wharton's jelly, a method for preparing them, and the therapeutic uses thereof, in particular for the treatment of sepsis.

BACKGROUND

Although often little known, septic shock represents, in tandem with myocardial infarction, the eleventh leading cause of death worldwide. The leading cause of admission and death in non-coronary resuscitation unit, its incidence is between 50 and 100 cases per 100,000 inhabitants and has continued to grow in recent years (Dombrovskiy et al., 2007). The increase in life expectancy, the growing number of multidrug-resistant bacteria and more frequent diagnosis are at the origin of this phenomena.

The physiopathology of septic shock is particularly complex (Iskander et al., 2013) and involves both pro-inflammatory and anti-inflammatory cytokines simultaneously, as well as immunoparalysis. There is no specific treatment for septic shock due to the inability of conventional pharmaceutical molecules to act on both the inflammatory aspect and on the anti-inflammatory aspect, while boosting the immune system.

However, numerous studies using mouse models of endotoxaemia and peritonitis have revealed the ability of mesenchymal stem cells (MSC) to reduce plasma levels of IL6, IL1β, IL12, IL2 and IL17 (Chao et al., 2014a; Kim et al., 2014; Luo et al., 2014; Pedrazza et al., 2014) and to lower the tissular concentration of TNFα, IL6, IL1β, IL12 in the lungs, liver and intestine (Gonzalez-Rey et al., 2009), or in the bronchoalveolar fluid (Mei et al., 2010a).

The ability of MSC to limit the tissular migration of neutrophiles helps to moderate the deleterious effects of inflammation on the tissues (Rojas et al., 2014). Studies of histological sections of mice subject to polymicrobial sepsis by caecal ligation and puncture (CLP) or subject to a sepsis by endotoxaemia, show a reduction in inflammation of the pulmonary and renal tissues when treated with MSC (Krasnodembskaya et al., 2010). Similarly, these mice present biological markers of the functional organs such as amylasemia, creatininemia, bilirubinemia, aspartate aminotransferases (ASAT) and alanine aminotransferases (ALAT) that are significantly better than mice treated by a saline solution (Luo et al., 2014; Pedrazza et al., 2014).

In addition to their ability to limit tissue alteration, MSC are capable of increasing bacterial clearance during septic shock. Indeed, several teams have demonstrated that the injection of MSC into septic mice resulted in the reduction of bacteraemia by increasing the phagocytic activity of the monocytes, macrophages and neutrophiles, but also through synthesis and secretion by the MSC themselves of antibacterial peptides such as LL-37 and hepcidin (Alcayaga-Miranda et al., 2015; Devaney et al., 2015; Gonzalez-Rey et al., 2009; Hall et al., 2013; Krasnodembskaya et al., 2010; Mei et al., 2010b).

Furthermore, the MSC exhibit intrinsic "homing" properties which give them a tendency to migrate along a chemokine gradient towards injured organs such as the liver, the kidneys and the lungs. This ability to reach the damaged tissues is a particularly interesting property of MSC in the context of an organ failure pathology such as septic shock (Wannemuehler et al., 2012).

Finally, the reduction of tissue lesions through the injection of MSC in mouse models of severe sepsis leads to an increase in survival. Many studies reveal a significant reduction in the mortality of animals treated by MSC pre- or post-sepsis (Alcayaga-Miranda et al., 2015; Devaney et al., 2015; Gonzalez-Rey et al., 2009; Krasnodembskaya et al., 2012; Luo et al., 2014; Nemeth et al., 2009). Thus, through their ability to regulate hyper-inflammation and to moderate tissue lesions, MSC appear to be able to significantly improve post-septic shock survival.

There are three major sources of MSC: bone marrow (BM), the adipose tissue and Wharton's jelly (WG) of the umbilical cord. Compared with MSC from BM, MSC from WG obtained in a simple, non-invasive manner without anaesthesia, makes it possible to apply MSC donation more generally, by overcoming the risk related to BM collection. However, whereas MSC from BM or MSC from adipose tissue have been studied in septic shock animal models, the potential of MSC from Wharton's jelly in this respect remains poorly documented.

To date, only five publications have analysed the therapeutic potential of WG-MSC on septic shock by using a mouse model of CLP (Chao et al., 2014a; Condor et al., 2016; Wu et al., 2015; Zhao et al., 2014). However, the cells used in these studies are fresh cells. No study published to date relate to thawed WG-MSC in the indication of septic shock, maybe due to the general knowledge of the freezing and thawing impact on the pharmacological and immunomodulatory potential of stem cells (Francois et al., Cytotherapy, 2012.14(2):147-52; Chinnadurai et al., 2016; Moll et al., 2016).

Furthermore, Mezey and Nemeth (2015) have described a reduction in the antibacterial properties of MSC when they are injected late.

Consequently, currently, these technical constraints prevent the use of WG-MSC under clinical conditions for a therapeutic treatment.

Against all expectations, the Inventors of the present invention have shown for the first time that thawed WG-MSC retain their therapeutic potential and can be used in the treatment of sepsis.

SUMMARY

The present invention relates to thawed human mesenchymal stem cells (MSC) from Wharton's jelly, for their use in the treatment of sepsis, in particular septic shock.

In an embodiment, the thawed human MSC from Wharton's jelly of the present invention are characterised in that the expression level of at least one marker selected from CD90, CD73, CD105, CD29, CD44, CD146, CD166, HLA-ABC is at least 10% lower than the expression level of the same marker in fresh human MSC from Wharton's jelly.

In an embodiment, the thawed human MSC from Wharton's jelly of the present invention are characterised in that the expression level of the marker CD90 is at least 10% lower than the expression level of the marker CD90 in fresh human MSC from Wharton's jelly.

In an embodiment, the thawed human MSC from Wharton's jelly of the present invention are characterised in that said MSC express at least one protein selected from the group comprising ACTB, ANXA1, CAPZB, LASP1, PRDX2, PRDX3, PSA3, RS12 and SYWC.

In an embodiment, the thawed human MSC from Wharton's jelly of the present invention are characterised in that said MSC do substantially not express at least one protein selected from the group comprising ACTS, AL1B1, ANX10, GBB1, GBB2, GPRIN1, DTNA, MIPO1, PSB3 and PSDE.

In an embodiment, the thawed human MSC from Wharton's jelly of the present invention are characterised in that said MSC, in in vitro condition and/or in non-inflammatory condition, secrete at least one growth factor selected from BMP-7, IGFBP-1, insulin, FGF-7, NT-4 and VEGF-D.

In an embodiment, the thawed human MSC from Wharton's jelly of the present invention are characterised in that said MSC, in in vivo condition and/or in inflammatory condition, secrete at least one growth factor selected from BMP-7 and TGFβ3.

In an embodiment, the thawed human MSC from Wharton's jelly of the present invention are characterised in that said MSC, in in vivo condition and/or in inflammatory condition, do substantially not secrete IGFBP-1.

In an embodiment, the thawed human MSC from Wharton's jelly of the present invention are characterised in that said MSC secrete at least 1.2 times more VEGF than fresh human MSC from Wharton's jelly.

In an embodiment, the thawed human MSC from Wharton's jelly of the present invention are characterised in that said MSC induce an increase in the VEGF seric concentration in patients, by at least 5% with respect to fresh human MSC from Wharton's jelly.

In an embodiment, the thawed human MSC from Wharton's jelly of the present invention are characterised in that said cells are obtained from the human umbilical cord tissue coming from a mother meeting at least one of the following criteria: having received an administration of oxytocin during childbirth, having given birth by directed labour, having given birth at term, not having presented pre-eclampsia during the pregnancy, whose child has not presented neonatal disorders and having been subject to an intake of tobacco smoke during the pregnancy In an embodiment, the thawed human MSC from Wharton's jelly of the present invention are characterised in that said MSC are clinical grade cells.

In an embodiment, the thawed human MSC from Wharton's jelly of the present invention are characterised in that said cells are obtained directly from thawing without reculturing after thawing.

The present invention also relates to a pharmaceutical composition comprising thawed human MSC from Wharton's jelly according to the present invention and a pharmaceutically acceptable excipient, for use in the treatment of sepsis.

The present invention also relates to a method for preparing clinical grade mesenchymal stem cells from Wharton's jelly, comprising the following steps:
(i) cultivating a human umbilical cord tissue containing Wharton's jelly in a clinical grade culture medium for cell adhesion;
(ii) incubating the adherent cells in a medium containing platelet lysate; characterised in that said tissue comes from a mother meeting at least one of the following criteria: having received an administration of oxytocin during childbirth, having given birth by directed labour, having given birth at term, not having presented pre-eclampsia during the pregnancy, whose child has not presented neonatal disorders and having been subject to an intake of tobacco smoke during the pregnancy.

BRIEF DESCRIPTION OF THE DRAWINGS

The present invention is illustrated in more detail in the figures and examples described below.

DETAILED DESCRIPTION

Figure 1:
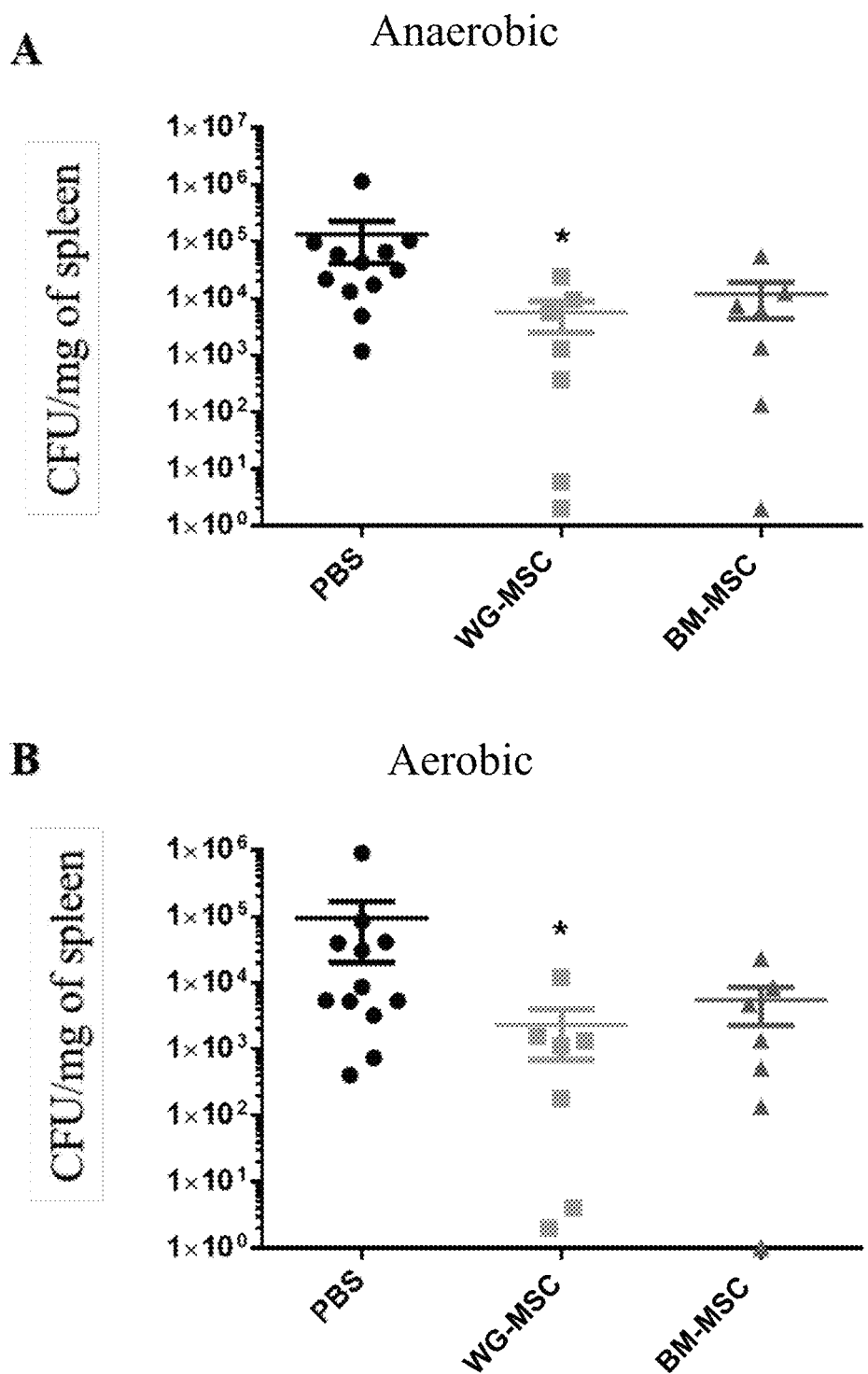
FIGS. 1A and B: these figures show, respectively, the mean number of CFU in anaerobic condition (A) or in aerobic condition (B) per milligram of spleen. The results are shown as mean±SEM. n=7-12 mice per group. *$p<0.05$ MSC versus PBS.

In the present invention, the terms below are defined in the following manner:

"Absence of neonatal disorders" shall mean the fact that a newborn presents no sign of prematurity, nor of intrauterine growth restriction, nor of foetal distress. The prematurity is determined by the number of weeks of amenorrhoea. The intrauterine growth restriction is determined by the birth weight, the size at birth and the head circumference. The foetal distress is determined by the arterial pH of the umbilical cord blood and the Apgar score defined by A=appearance (colouration), P=pulse, G=grimace (reflexes to stimuli), A=activity (muscle tone), R=respiration (respiratory effort). The thresholds for these parameters for determining that the newborn does not present neonatal disorders are well known to a person skilled in the art.

"Giving birth at term" shall mean a labour giving birth to a newborn having a birth weight greater than 3.2 kg, after at least 39.5 weeks of amenorrhoea, and the weight of the placenta at the time of delivery being greater than 550 grams.

"Giving birth by directed labour" shall mean a labour assisted by administration of oxytocin or artificial rupture of the amniotic sac.

"Clinical grade cells" shall mean cells having had no contact with a substance of non-human animal origin, such as non-human animal serum, during isolation, culture, cryopreservation and thawing of the cells. Clinical grade cells are cells produced under culture conditions compatible with use in humans and conforming with the Good Practices of pharmaceutical production.

"Cryopreserved stem cells" shall mean stem cells preserved at very low temperature, preferably between −150° C. and −196° C., preferably in the presence of a cryoprotectant solution containing dimethyl sulfoxide (DMSO).

"Mesenchymal stem cells" shall mean multipotent stem cells of mesodermic origin, found in various tissues of the adult organism such as the bone marrow, adipose tissue and umbilical cord. These stromal cells are capable of self-renewal and differentiation into at least osteoblast, chondrocyte and adipocyte cell lines, including without limitation, cells of the bone, cartilage, adipose tissue and medullary stroma, smooth muscle, ligaments and tendons.

"Thawed human mesenchymal stem cells" shall mean mesenchymal stem cells isolated from human tissue and having undergone a thawing process of cryopreserved stem cells.

"Fresh human mesenchymal stem cells" shall mean mesenchymal stem cells isolated from human tissues and not having undergone a freeze-thaw process.

"Wharton's jelly" shall mean the connective tissue of extra-embryonic mesoblast origin, enveloping the two arteries of the umbilical vein and thus protecting the umbilical cord "Sepsis" shall mean a general severe infection of the organism by pathogenic microorganisms, in particular bacteria. Sepsis is defined as an organ dysfunction secondary to an inappropriate response of the organism to an infection. Depending on the severity, the septic state can be classified into two orders: sepsis stricto sensu, and septic shock ("The Third International Consensus Definitions for Sepsis and Septic Shock (Sepsis-3)", JAMA. 2016; 315(8): 801-810). Sepsis, according to the narrowest definition, clinically associates an infection with a SOFA score (Sequential Organ Failure Assessment Score)≥2 or an increase in the SOFA score greater than or equal to 2 points if an organ dysfunction existed before infection. Septic shock, associates a sepsis with the need to use vasopressors q.s.f. MAP [mean arterial pressure]≥65 mmHg and/or a lactatemia >2 mmol/L (i.e., 18 mg/dL), and this, despite an adequate vascular filling.

The present invention relates to mesenchymal stem cells (MSC) for use in the treatment of sepsis, in particular septic shock.

In an embodiment, the MSC are animal stem cells, preferably mammals stem cells, more preferably human stem cells. In a particular embodiment, the MSC are human stem cells.

In an embodiment, the MSC are from Wharton's jelly, from the bone marrow and/or from adipose tissue. In an embodiment, the MSC are from Wharton's jelly. In an embodiment, the MSC are from bone marrow. In an embodiment, the MSC are from adipose tissue. Preferably, the MSC are from Wharton's jelly.

In an embodiment, the MSC are thawed, i.e., they have undergone a freeze-thaw process.

More particularly, the present invention therefore relates to thawed human mesenchymal stem cells from Wharton's jelly (WG-MSC), for use in the treatment of sepsis, in particular septic shock.

In an embodiment, the thawed MSC, preferably thawed WG-MSC, have phenotypic features different from fresh MSC, preferably fresh WG-MSC.

In an embodiment, the thawed MSC, preferably thawed WG-MSC, are characterised in that:
  at least 60% of cells express the following antigens: CD90, CD73, CD105, CD44; and
  at least 80% of cells express none of the following markers: CD34, CD11b, CD19, CD45, HLA-DR; and
  at least 10% of the cells express the marker CD106.

In an embodiment, the thawed MSC, preferably thawed WG-MSC, are characterised in that:
  at least 60% of cells express the following antigens: CD90, CD73, CD105, CD44; and
  at least 80% of cells express none of the following markers: CD34, CD11 b, CD19, CD45, CD144, HLA-DR; and
  at least 10% of the cells express the marker CD106.

In an embodiment, the thawed MSC, preferably thawed WG-MSC, are characterised in that the expression level of at least one marker selected from CD90, CD73, CD105, CD29, CD44, CD146, CD166, HLA-ABC is at least 5%, at least 10%, at least 15%, at least 20%, at least 25%, at least 30%, at least 35%, at least 40%, at least 45%, at least 50% or more lower than the expression level of the same marker in fresh MSC, preferably in fresh WG-MSC.

In an embodiment, the thawed MSC, preferably thawed WG-MSC, are characterised in that the expression level of the marker CD90 is at least 5%, at least 10%, at least 15%, at least 20%, at least 25%, at least 30%, at least 35%, at least 40%, at least 45%, at least 50% or more lower than the expression level of the marker CD90 in fresh MSC, preferably in fresh WG-MSC.

"CD90" shall mean the membrane glycoprotein Thy-1, an example of which is the human protein CD90, the UniProtKB accession number of which is P04216.

In an embodiment, the thawed MSC, preferably thawed WG-MSC, are characterised in that the expression level of the marker CD73 is at least 5%, at least 10%, at least 15%, at least 20%, at least 25%, at least 30%, at least 35%, at least 40%, at least 45%, at least 50% or more lower than the expression level of the marker CD73 in fresh MSC, preferably in fresh WG-MSC.

"CD73" shall mean the ecto-5'nucleotidase enzyme (or NTSE), an example of which is the human protein CD73, the UniProtKB accession number of which is P21589.

In an embodiment, the thawed MSC, preferably thawed WG-MSC, are characterised in that the expression level of the marker CD105 is at least 5%, at least 10%, at least 15%, at least 20%, at least 25%, at least 30%, at least 35%, at least 40%, at least 45%, at least 50% or more lower than the expression level of the marker CD105 in fresh MSC, preferably in fresh WG-MSC.

"CD105" shall mean the membrane glycoprotein endoglin, an example of which is the human protein CD105, the UniProtKB accession number of which is P17813.

In an embodiment, the thawed MSC, preferably thawed WG-MSC, are characterised in that the expression level of the marker CD29 is at least 5%, at least 10%, at least 15%, at least 20%, at least 25%, at least 30%, at least 35%, at least 40%, at least 45%, at least 50% or more lower than the expression level of the marker CD29 in fresh MSC, preferably in fresh WG-MSC.

"CD29" shall mean the protein integrin 0-1, an example of which is the human protein CD29, the UniProtKB accession number of which is P05556.

In an embodiment, the thawed MSC, preferably thawed WG-MSC, are characterised in that the expression level of the marker CD44 is at least 5%, at least 10%, at least 15%, at least 20%, at least 25%, at least 30%, at least 35%, at least 40%, at least 45%, at least 50% or more lower than the expression level of the marker CD44 in fresh MSC, preferably in fresh WG-MSC.

"CD44" shall mean the hyaluronan receptor, an example of which is the human protein CD44, the UniProtKB accession number of which is P16070.

In an embodiment, the thawed MSC, preferably thawed WG-MSC, are characterised in that the expression level of the marker CD146 is at least 5%, at least 10%, at least 15%, at least 20%, at least 25%, at least 30%, at least 35%, at least 40%, at least 45%, at least 50% or more lower than the expression level of the marker CD146 in fresh MSC, preferably in fresh WG-MSC.

"CD146" shall mean the melanoma cell adhesion molecule (MCAM) an example of which is the human protein CD146, the UniProtKB accession number of which is P43121.

In an embodiment, the thawed MSC, preferably thawed WG-MSC, are characterised in that the expression level of the marker CD166 is at least 5%, at least 10%, at least 15%, at least 20%, at least 25%, at least 30%, at least 35%, at least 40%, at least 45%, at least 50% or more lower than the expression level of the marker CD166 in fresh MSC, preferably in fresh WG-MSC.

"CD166" shall mean the Activated Leukocyte Cell Adhesion Molecule (ALCAM) an example of which is the human protein CD166, the UniProtKB accession number of which is Q13740.

In an embodiment, the thawed MSC, preferably thawed WG-MSC, are characterised in that the expression level of the marker HLA-ABC is at least 5%, at least 10%, at least 15%, at least 20%, at least 25%, at least 30%, at least 35%, at least 40%, at least 45%, at least 50% or more lower than the expression level of the marker HLA-ABC in fresh MSC, preferably in fresh WG-MSC.

"HLA-ABC" shall mean the surface receptors of the major histocompatibility complex class I, an example of which is human HLA-ABC, the UniProtKB accession number of which is 019689.

In an embodiment, the thawed MSC, preferably thawed WG-MSC, are characterised in that the expression level of at least one marker selected from CD13 and Sox-2 is at least 5%, at least 10%, at least 15%, at least 20%, at least 25%, at least 30%, at least 35%, at least 40%, at least 45%, at least 50% or more higher than the expression level of the same marker in fresh MSC, preferably in fresh WG-MSC.

In an embodiment, the thawed MSC, preferably thawed WG-MSC, are characterised in that the expression level of the marker CD13 is at least 5%, at least 10%, at least 15%, at least 20%, at least 25%, at least 30%, at least 35%, at least 40%, at least 45%, at least 50% or more higher than the expression level of the marker CD13 in fresh MSC, preferably in fresh WG-MSC.

"CD13" shall mean membrane alanyl aminopeptidase, an example of which is the human protein CD13, the UniProtKB accession number of which is P15144.

In an embodiment, the thawed MSC, preferably thawed WG-MSC, are characterised in that the expression level of the marker Sox-2 is at least 5%, at least 10%, at least 15%, at least 20%, at least 25%, at least 30%, at least 35%, at least 40%, at least 45%, at least 50% or more higher than the expression level of the marker Sox-2 in fresh MSC, preferably in fresh WG-MSC.

"Sox-2" shall mean transcription factor SRY-box 2, an example of which is the human protein Sox-2, the UniProtKB accession number of which is P48431.

In an embodiment, the thawed MSC, preferably thawed WG-MSC, after at least one passage in subculture, are characterised in that the expression level of at least one marker selected from CD44 and SSEA-4 is at least 5%, at least 10%, at least 15%, at least 20%, at least 25%, at least 30%, at least 35%, at least 40%, at least 45%, at least 50% or more lower than the expression level of the same marker in fresh MSC, preferably in fresh WG-MSC.

In an embodiment, the thawed MSC, preferably thawed WG-MSC, after at least one passage in subculture, are characterised in that the expression level of the marker CD44 is at least 5%, at least 10%, at least 15%, at least 20%, at least 25%, at least 30%, at least 35%, at least 40%, at least 45%, at least 50% or more lower than the expression level of the marker CD44 in fresh MSC, preferably in fresh WG-MSC.

In an embodiment, the thawed MSC, preferably thawed WG-MSC, after at least one passage in subculture, are characterised in that the expression level of the marker SSEA-4 is at least 5%, at least 10%, at least 15%, at least 20%, at least 25%, at least 30%, at least 35%, at least 40%, at least 45%, at least 50% or more lower than the expression level of the marker SSEA-4 in fresh MSC, preferably in fresh WG-MSC.

"SSEA-4" shall mean the membrane ganglioside consisting of a glycosphingolipid comprising a terminal sialic acid residue (Stage-Specific Embryonic Antigen 4).

In an embodiment, the thawed MSC, preferably thawed WG-MSC, after at least one passage in subculture, are characterised in that the expression level of at least one marker selected from CD90, CD166 and HLA-ABC is at least 5%, at least 10%, at least 15%, at least 20%, at least 25%, at least 30%, at least 35%, at least 40%, at least 45%, at least 50% or more higher than the expression level of the same marker in fresh MSC, preferably in fresh WG-MSC.

In an embodiment, the thawed MSC, preferably thawed WG-MSC, after at least one passage in subculture, are characterised in that the expression level of the marker CD90 is at least 5%, at least 10%, at least 15%, at least 20%, at least 25%, at least 30%, at least 35%, at least 40%, at least 45%, at least 50% or more higher than the expression level of the marker CD90 in fresh MSC, preferably in fresh WG-MSC.

In an embodiment, the thawed MSC, preferably thawed WG-MSC, after at least one passage in subculture, are characterised in that the expression level of the marker CD166 is at least 5%, at least 10%, at least 15%, at least 20%, at least 25%, at least 30%, at least 35%, at least 40%, at least 45%, at least 50% or more higher than the expression level of the marker CD166 in fresh MSC, preferably in fresh WG-MSC.

In an embodiment, the thawed MSC, preferably thawed WG-MSC, after at least one passage in subculture, are characterised in that the expression level of the marker HLA-ABC is at least 5%, at least 10%, at least 15%, at least 20%, at least 25%, at least 30%, at least 35%, at least 40%, at least 45%, at least 50% or more higher than the expression level of the marker HLA-ABC in fresh MSC, preferably in fresh WG-MSC.

In an embodiment, the expression level of markers is measured by methods that are well known to a person skilled in the art. In an embodiment, the expression level of markers is measured by flow cytometry. In an embodiment, the expression level of markers is measured by mean fluorescence intensity (MFI).

In an embodiment, the thawed MSC, preferably thawed WG-MSC, are characterised by a differential protein expression with respect to fresh MSC, preferably fresh WG-MSC.

In an embodiment, the thawed MSC, preferably thawed WG-MSC, express at least one protein selected from the group comprising or consisting of ACTB (cytoplasmic actin 1), ANXA1 (annexin A1), CAPZB (F-actin-capping protein subunit beta), LASP1 (LIM and SH3 domain protein 1), PRDX2 (peroxiredoxin-2), PRDX3 (mitochondrial thioredoxin-dependent peroxide reductase), PSA3 (proteasome subunit alpha type-3), RS12 (40S ribosomal protein S12) and SYWC (cytoplasmic tryptophan-tRNA ligase).

In an embodiment, the fresh MSC, preferably fresh WG-MSC, do not express or do substantially not express at least one protein selected from the group comprising or consisting of ACTB (cytoplasmic actin 1), ANXA1 (annexin A1), CAPZB (F-actin-capping protein subunit beta), LASP1 (LIM and SH3 domain protein 1), PRDX2 (peroxiredoxin-2), PRDX3 (mitochondrial thioredoxin-dependent peroxide reductase), PSA3 (proteasome subunit alpha type-3), RS12 (40S ribosomal protein S12) and SYWC (cytoplasmic tryptophan-tRNA ligase).

In an embodiment, the thawed MSC, preferably thawed WG-MSC, express at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times more of at least one protein selected from the group comprising or consisting of ACTB (cytoplasmic actin 1), ANXA1 (annexin A1), CAPZB (F-actin-capping protein subunit beta), LASP1 (LIM and SH3 domain protein 1), PRDX2 (peroxiredoxin-2), PRDX3 (mitochondrial thioredoxin-dependent peroxide reductase), PSA3 (proteasome subunit alpha type-3), RS12 (40S ribosomal protein S12) et SYWC (cytoplasmic tryptophan-tRNA ligase), than fresh MSC, preferably than fresh WG-MSC.

"ACTB" shall mean the protein cytoplasmic actin 1, an example of which is human ACTB, the UniProtKB accession number of which is P60709.

"ANXA1" shall mean the protein annexin 1, an example of which is human ANXA1, the UniProtKB accession number of which is P04083.

"CAPZB" shall mean the F-actin-capping protein subunit beta, an example of which is human CAPZB, the UniProtKB accession number of which is P47756.

"LASP1" shall mean LIM and SH3 domain protein 1, an example of which is human LASP1, the UniProtKB accession number of which is Q14847.

"PRDX2", shall mean peroxiredoxin 2, an example of which is human PRDX2, the UniProtKB accession number of which is P32119.

"PRDX3" shall mean peroxiredoxin 3 (mitochondrial thioredoxin-dependent peroxide reductase), an example of which is human PRDX3, the UniProtKB accession number of which is P30048.

"PSA3" shall mean proteasome subunit alpha type-3, an example of which is human PSA3, the UniProtKB accession number of which is P25788.

"RS12" shall mean the 40S ribosomal protein S12, an example of which is human RS12, the UniProtKB accession number of which is P25398.

"SYWC" shall mean cytoplasmic tryptophan-tRNA ligase, an example of which is human SYWC, the UniProtKB accession number of which is P23381.

In an embodiment, the thawed MSC, preferably thawed WG-MSC, do not express or do substantially not express at least one protein selected from the group comprising or consisting of ACTS (skeletal muscle alpha actin), AL1B1 (mitochondrial aldehyde dehydrogenase X), ANX10 (annexin A10), GBB1 (guanine nucleotide-binding protein G(I)/G(S)/G(T) subunit beta-1), GBB2 (guanine nucleotide-binding protein G(I)/G(S)/G(T) subunit beta-2), GPRIN1 (G protein-regulated inducer of neurite outgrowth 1), DTNA (dystrobrevin alpha), MIPO1 (mirror-image polydactyly gene 1 protein), PSB3 (proteasome subunit beta type-3) and PSDE (26S proteasome non-ATPase regulatory subunit 14).

In an embodiment, the fresh MSC, preferably fresh WG-MSC, express at least one protein selected from the group comprising or consisting of ACTS (skeletal muscle alpha actin), AL1B1 (mitochondrial aldehyde dehydrogenase X), ANX10 (annexin A10), GBB1 (guanine nucleotide-binding protein G(I)/G(S)/G(T) subunit beta-1), GBB2 (guanine nucleotide-binding protein G(I)/G(S)/G(T) subunit beta-2), GPRIN1 (G protein-regulated inducer of neurite outgrowth 1), DTNA (dystrobrevin alpha), MIPO1 (mirror-image polydactyly gene 1 protein), PSB3 (proteasome subunit beta type-3) and PSDE (26S proteasome non-ATPase regulatory subunit 14).

In an embodiment, the thawed MSC, preferably thawed WG-MSC, express at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times less of at least one protein selected from the group comprising or consisting of ACTS (skeletal muscle alpha actin), AL1B1 (mitochondrial aldehyde dehydrogenase X), ANX10 (annexin A10), GBB1 (guanine nucleotide-binding protein G(I)/G(S)/G(T) subunit beta-1), GBB2 (guanine nucleotide-binding protein G(I)/G(S)/G(T) subunit beta-2), GPRIN1 (G protein-regulated inducer of neurite outgrowth 1), DTNA (dystrobrevin alpha), MIPO1 (mirror-image polydactyly gene 1 protein), PSB3 (proteasome subunit beta type-3) and PSDE (26S proteasome non-ATPase regulatory subunit 14), than fresh MSC, preferably fresh WG-MSC.

"ACTS" shall mean the protein skeletal muscle alpha actin, an example of which is human ACTS, the UniProtKB accession number of which is P68133.

"AL1B1" shall mean mitochondrial aldehyde dehydrogenase X, an example of which is human AL1B1, the UniProtKB accession number of which is P30837.

"ANX10" shall mean annexin A10, an example of which is human ANX10, the UniProtKB accession number of which is Q9UJ72.

"GBB1" shall mean guanine nucleotide-binding protein G(I)/G(S)/G(T) subunit beta-1, an example of which is human GBB1, the UniProtKB accession number of which is P62873.

"GBB2" shall mean guanine nucleotide-binding protein G(I)/G(S)/G(T) subunit beta-2, an example of which is human GBB2, the UniProtKB accession number of which is P62879.

"GPRIN1" shall mean the G protein-regulated inducer of neurite outgrowth 1, an example of which is human GPRIN1, the UniProtKB accession number of which is Q7Z2K8.

"DTNA" shall mean dystrobrevin alpha, an example of which is human DTNA, the UniProtKB accession number of which is Q9Y4J8.

"MIPO1" shall mean mirror-image polydactyly gene 1 protein, an example of which is human MrPO1, the UniProtKB accession number of which is Q8TD10.

"PSB3" shall mean proteasome subunit beta type-3, an example of which is human PSB3, the UniProtKB accession number of which is P49720.

"PSDE" shall mean 26S proteasome non-ATPase regulatory subunit 14, an example of which is human PSDE, the UniProtKB accession number of which is O00487.

In an embodiment, the thawed MSC, preferably thawed WG-MSC, after at least 1 passage in sub-culture, express at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times more of at least one protein selected from the group comprising or consisting of AMPM2 (methionine aminopeptidase 2), DJB11 (dnaJ homolog subfamily B member 11), K1C18 (keratin, type I cytoskeletal 18), K1C19 (keratin, type I cytoskeletal 19), K2C8 (keratin type II cytoskeletal 8), LYSC (lysozyme C), PDIA3 (protein disulfide-isomerase A3), TCTP (translationally-controlled tumour protein) and TGM2 (protein-glutamine gamma-glutamyltransferase 2) than fresh MSC, preferably than fresh WG-MSC.

"AMPM2" shall mean methionine aminopeptidase 2, an example of which is human AMPM2, the UniProtKB accession number of which is P50579.

"DJB11" shall mean dnaJ homolog subfamily B member 11, an example of which is human DJB11, the UniProtKB accession number of which is Q9UBS4.

"K1C18" shall mean keratin, type I cytoskeletal 18, an example of which is human K1C18, the UniProtKB accession number of which is P05783.

"K1C19" shall mean keratin, type I cytoskeletal 19, an example of which is human K1C19, the UniProtKB accession number of which is P08727.

"K2C8" shall mean keratin type II cytoskeletal 8, an example of which is human K2C8, the UniProtKB accession number of which is P05787.

"LYSC" shall mean lysozyme C, an example of which is human LYSC, the UniProtKB accession number of which is P61626.

"PDIA3" shall mean protein disulfide-isomerase A3, an example of which is human PDIA3, the UniProtKB accession number of which is P30101.

"TCTP" shall mean translationally-controlled tumour protein, an example of which is human TCTP, the UniProtKB accession number of which is P13693.

"TGM2" shall mean the enzyme protein-glutamine gamma-glutamyltransferase 2, an example of which is human TGM2, the UniProtKB accession number of which is P21980.

In an embodiment, the thawed MSC, preferably thawed WG-MSC, after at least one passage in sub-culture, express at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times less of at least a protein selected from the group comprising or consisting of GSTP1 (glutathione S-transferase P), HSP7C (heat shock cognate 71 kDa protein), HS (heat shock protein beta-1), LEG1 (galectin-1), S10AB (protein S100-A11) and UBE2N (ubiquitin-conjugating enzyme E2 N), than fresh MSC, preferably than fresh WG-MSC.

"GSTP1" shall mean the enzyme glutathione 5-transferase P, an example of which is human GSTP1, the UniProtKB accession number of which is P09211.

"HSP7C" shall mean heat shock cognate 71 kDa protein, an example of which is human HSP7C, the UniProtKB accession number of which is P11142.

"HSPB1" heat shock protein beta-1, an example of which is human HSPB1, the UniProtKB accession number of which is P04792.

"LEG1" shall mean galectin-1, an example of which is human LEG1, the UniProtKB accession number of which is P09382.

"S10AB" shall mean protein S100-A11, an example of which is human S10AB, the UniProtKB accession number of which is P31949.

"UBE2N" shall mean ubiquitin-conjugating enzyme E2 N, an example of which is human UBE2N, the UniProtKB accession number of which is P61088.

In an embodiment, the protein expression is measured by methods that are well known to a person skilled in the art. In an embodiment, the protein expression is measured by mass spectrometry.

In an embodiment, the thawed MSC, preferably thawed WG-MSC, in in vitro condition and/or in non-inflammatory condition, secrete at least one growth factor selected from BMP-7, IGFBP-1, insulin, FGF-7, NT-4 and VEGF-D.

In an embodiment, the thawed MSC, preferably thawed WG-MSC, in in vitro condition and/or in non-inflammatory condition, secrete at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times more of at least one growth factor selected from BMP-7, IGFBP-1, insulin, FGF-7, NT-4 and VEGF-D, than fresh MSC, preferably than fresh WG-MSC in in vitro condition and/or in non-inflammatory condition.

In an embodiment, the thawed MSC, preferably thawed WG-MSC, in in vitro condition and/or in non-inflammatory condition, secrete at least 50 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL or more of BMP-7.

In an embodiment, the thawed MSC, preferably thawed WG-MSC, in in vitro condition and/or in non-inflammatory condition, secrete at least 20 pg/mL, at least 25 pg/mL, at least 30 pg/mL, at least 35 pg/mL, at least 40 pg/mL, at least 45 pg/mL, at least 50 pg/mL, at least 55 pg/mL, at least 60 pg/mL, at least 65 pg/mL or more of IGFBP-1.

In an embodiment, the thawed MSC, preferably thawed WG-MSC, in in vitro condition and/or in non-inflammatory condition, secrete at least 50 pg/mL, at least 75 pg/mL, at least 100 pg/mL, at least 125 pg/mL, at least 150 pg/mL, at least 175 pg/mL, at least 200 pg/mL, at least 225 pg/mL, at least 250 pg/mL, at least 275 pg/mL or more of insulin.

In an embodiment, the thawed MSC, preferably thawed WG-MSC, in in vitro condition and/or in non-inflammatory condition, secrete at least 10 pg/mL, at least 15 pg/mL at least 20 pg/mL, at least 25 pg/mL, at least 30 pg/mL, at least 35 pg/mL, at least 40 pg/mL, at least 45 pg/mL, at least 50 pg/mL, at least 55 pg/mL, at least 60 pg/mL, at least 65 pg/mL or more of FGF-7.

In an embodiment, the thawed MSC, preferably thawed WG-MSC, in in vitro condition and/or in non-inflammatory condition, secrete at least 45 pg/mL, at least 50 pg/mL, at least 55 pg/mL, at least 60 pg/mL, at least 65 pg/mL, at least 70 pg/mL, at least 75 pg/mL, at least 80 pg/mL, at least 85 pg/mL, at least 90 pg/mL or more of NT-4.

In an embodiment, the thawed MSC, preferably thawed WG-MSC, in in vitro condition and/or in non-inflammatory condition, secrete at least 5 pg/mL, at least 10 pg/mL, at least 15 pg/mL, at least 20 pg/mL, at least 25 pg/mL, at least 30 pg/mL, at least 35 pg/mL, at least 40 pg/mL, at least 45 pg/mL, at least 50 pg/mL or more of VEGF-D.

In an embodiment, the thawed MSC, preferably thawed WG-MSC, in in vivo condition and/or in inflammatory condition, secrete at least one growth factor selected from BMP-7 and TGFβ3.

In an embodiment, the thawed MSC, preferably thawed WG-MSC, in in vivo condition and/or in inflammatory condition, secrete at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times more of at least one growth factor selected from BMP-7 and TGFβ3, than fresh MSC, preferably than fresh WG-MSC in in vivo condition and/or in inflammatory condition.

In an embodiment, the thawed MSC, preferably thawed WG-MSC, in in vivo condition and/or in inflammatory condition, secrete at least 200 pg/mL, at least 250 pg/mL at least 300 pg/mL, at least 350 pg/mL, at least 400 pg/mL, at least 450 pg/mL, at least 500 pg/mL, at least 550 pg/mL, at least 600 pg/mL, at least 650 pg/mL, at least 700 pg/mL, at least 750 pg/mL or more of BMP-7.

In an embodiment, the thawed MSC, preferably thawed WG-MSC, in in vivo condition and/or in inflammatory condition, secrete at least 20 pg/mL, at least 25 pg/mL, at least 30 pg/mL, at least 35 pg/mL, at least 40 pg/mL, at least 45 pg/mL, at least 50 pg/mL, at least 55 pg/mL, at least 60 pg/mL, at least 65 pg/mL or more of TGFβ3.

In an embodiment, the thawed MSC, preferably thawed WG-MSC, in in vivo condition and/or in inflammatory condition, do not secrete or do substantially not secrete IGFBP-1.

In an embodiment, the thawed MSC, preferably thawed WG-MSC, in in vivo condition and/or in inflammatory condition, secrete at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times less IGFBP-1 than fresh MSC, preferably than fresh WG-MSC in in vivo condition and/or in inflammatory condition.

In an embodiment, the thawed MSC, preferably thawed WG-MSC, in in vivo condition and/or in inflammatory condition, secrete less than 20 pg/mL, at least 15 pg/mL, at least 10 pg/mL, at least 5 pg/mL, at least 4 pg/mL, at least 3 pg/mL, at least 2 pg/mL, at least 1 pg/mL or less IGFBP-1.

"BMP-7" shall mean bone morphogenetic protein 7. An example of BMP-7 is human BMP-7 protein, the UniProtKB accession number of which is P18075.

"IGFBP-1" shall mean insulin-like growth factor-binding protein 1. An example of IGFBP-1 is human IGFBP-1 protein, the UniProtKB accession number of which is P08833.

"Insulin" shall mean the protein hormone promoting the absorption of blood glucose. An example of insulin is human insulin, the UniProtKB accession number of which is P01308.

"FGF-7" shall mean fibroblast growth factor 7. An example of FGF-7 is human FGF-7 protein, the UniProtKB accession number of which is P21781.

"NT-4" shall mean neurotrophin 4. An example of NT-4 is human NT-4 protein, the UniProtKB accession number of which is P34130.

"VEGF-D" shall mean vascular endothelial growth factor D. An example of VEGF-D is human VEGF-D protein, the UniProtKB accession number of which is O43915.

"TGFβ3" shall mean transforming growth factor β3. An example of TGFβ3 is human TGFβ3 protein, the UniProtKB accession number of which is P10600.

"In vitro condition" shall mean a condition in which the thawed MSC, preferably thawed WG-MSC, are outside of a living organism, preferably outside of the patient.

"In vivo condition" shall mean a condition in which the thawed MSC, preferably thawed WG-MSC, are inside a living organism, preferably inside the patient, i.e., after their administration to the patient.

"Non-inflammatory condition" shall mean a condition in which the thawed MSC, preferably thawed WG-MSC are not stimulated, in vitro or in vivo, by inflammatory cytokines, including but not limited to TNF-α and IFN-γ. In particular, a non-inflammatory condition can be defined as a condition in vivo, preferably inside the patient, said patient being healthy or substantially healthy, i.e., said patient is not affected by a sepsis.

"Inflammatory condition" shall mean a condition in which the thawed MSC, preferably thawed WG-MSC are stimulated, in vitro or in vivo, by inflammatory cytokines, including but not limited to TNF-α and IFN-γ. In particular, an inflammatory condition can be defined as a condition in vivo, preferably inside the patient, said patient being affected by a sepsis.

In an embodiment, the thawed MSC, preferably thawed WG-MSC, secrete VEGF.

In an embodiment, the thawed MSC, preferably thawed WG-MSC, secrete at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times more VEGF than fresh MSC, preferably than fresh WG-MSC.

In an embodiment, the thawed MSC, preferably thawed WG-MSC, secrete at least 500 pg/mL, at least 600 pg/mL, at least 700 pg/mL, at least 800 pg/mL, at least 900 pg/mL, at least 1 ng/mL, at least 1.25 ng/mL, at least 1.5 ng/mL, at least 1.75 ng/mL, at least 2 ng/mL or more of VEGF.

In an embodiment, the thawed MSC, preferably thawed WG-MSC, do not secrete or do substantially not secrete VEGF.

In an embodiment, the thawed MSC, preferably thawed WG-MSC, secrete at least 1.1 times, 1.2 times, 1.3 times, 1.4 times, 1.5 times, 1.6 times, 1.7 times, 1.8 times, 1.9 times, 2 times, 2.5 times, 3.0 times, 3.5 times, 4.0 times, 4.5 times, 5.0 times, 7.5 times, 10.0 times, 15.0 times, 20.0 times, 30.0 times, 40.0 times, 50.0 times less VEGF than fresh MSC, preferably than fresh WG-MSC.

In an embodiment, the thawed MSC, preferably thawed WG-MSC, secrete less than 500 pg/mL, at least 400 pg/mL, at least 300 pg/mL, at least 250 pg/mL, at least 200 pg/mL, at least 150 pg/mL, at least 100 pg/mL, at least 50 pg/mL or less of VEGF.

"VEGF" shall mean vascular endothelial growth factor. An example of VEGF is human VEGF protein, the UniProtKB accession number of which is P15692.

In an embodiment, the thawed MSC, preferably thawed WG-MSC, in in vivo condition and/or in inflammatory condition, induce the secretion of VEGF.

Several cells can secrete VEGF. Examples of such cells include, without limitation, macrophages, monocytes, endothelial cells, myofibroblasts, chondrocytes, and haematopoietic cells.

In an embodiment, the thawed MSC, preferably thawed WG-MSC, induce an increase in the VEGF seric concentration of at least 5%, 10%, 15%, 20%, 25%, 30%, 35%, 40%, 45%, 50% or more, with respect to fresh MSC, preferably with respect to fresh WG-MSC.

In an embodiment, the thawed MSC, preferably thawed WG-MSC, induce an increase in the plasmatic concentration of VEGF of at least 5%, 10%, 15%, 20%, 25%, 30%, 35%, 40%, 45%, 50% or more, with respect to fresh MSC, preferably with respect to fresh WG-MSC.

In an embodiment, the MSC, preferably WG-MSC, are preserved at very low temperature. In an embodiment, the MSC, preferably WG-MSC, are preserved at about −° C., preferably at about −80° C., preferably between −150° C. and −196° C. In an embodiment, the MSC, preferably WG-MSC, are preserved in the presence of a cryoprotectant solution. Cryoprotectant solutions for cells are well known to a person skilled in the art. In one embodiment, the cryoprotectant solution comprises at least one cryoprotectant selected from dimethyl sulfoxide (DMSO), glycerol, ethylene glycol, propylene glycol, formamide, butene diol and mixtures thereof.

In an embodiment, the MSC, preferably WG-MSC, are thawed according to a conventional thawing protocol. By way of example, the MSC, preferably WG-MSC, are thawed in a water bath at 37° C., then washed in the presence of a washing solution comprising NaCl, albumin and acid citrate dextrose formula A (ACD).

A particular embodiment of the invention relates to thawed WG-MSC as described above, for use in the treatment of septic shock, the most severe form of sepsis, which is defined by the appearance or persistence of arterial hypotension and/or signs of peripheral hypoperfusion despite an adequate vascular filling.

In an advantageous embodiment, the MSC, preferably WG-MSC used in the invention are obtained directly from thawing, without reculturing after thawing.

In contrast to previous studies, in which the analysed cells were fresh cells, which had not been subjected to freezing or thawing, and were administered at an early time to the animals in a septic shock model, the results of the present invention provide evidence, for the first time, of the effectiveness of WG-MSC under conditions compatible with clinical conditions, namely the administration of thawed WG-MSC at a late time in the development of the sepsis.

The present invention demonstrates that thawed WG-MSC retain the immunomodulatory and antibacterial properties at a level comparable with thawed MSC cells isolated from bone marrow (BM-MSC) and the administration of WG-MSC makes it even possible to increase the survival of mice suffering from a septic shock compared with the survival of mice treated with BM-MSC.

These results show that the thawed WG-MSC are suitable for being used immediately under clinical conditions for the treatment of septic shock.

In an embodiment, the MSC, preferably WG-MSC used in the invention are washed after thawing. In an embodiment, the MSC, preferably WG-MSC used in the invention are returned to suspension after thawing. In an embodiment, the MSC, preferably WG-MSC used in the invention are returned to suspension after thawing in a hydroxyethyl starch solution. In an embodiment, the MSC, preferably WG-MSC used in the invention are returned to suspension after thawing in an albumin solution. In an embodiment, the albumin solution is a 4% albumin solution. In an embodiment, the albumin solution also comprises NaCl and/or acid citrate dextrose formula A (ACD).

In the present invention, the Inventors also observe, for the first time, a significant correlation between obstetric factors and the proliferation of WG-MSC, and provide the criteria for selecting umbilical cords in order to obtain WG-MSC having a better proliferation capacity.

One object of the invention relates to the WG-MSC from human umbilical cord tissue meeting these criteria.

It is observed that that these criteria improve cellular proliferation by reducing the doubling time of the number of cells, in particular at passage P1. These criteria also make it possible to obtain a larger number of cells with a short doubling time.

In an advantageous embodiment, the WG-MSC used in the present invention are from a human umbilical cord tissue which comes from a mother meeting at least one of the following criteria: having received an administration of oxytocin during childbirth, having given birth by directed labour, having given birth at term, not having presented pre-eclampsia during the pregnancy, whose child has not presented neonatal disorders and having been subject to an intake of tobacco smoke during the pregnancy.

The Inventors have observed that these obstetric factors have a positive impact on the cellular proliferation of MSC, preferably WG-MSC, and make it possible to select MSC, preferably WG-MSC, with better proliferation properties.

According to an embodiment, the MSC, preferably WG-MSC, used in the present invention, are clinical grade cells.

Consequently, any culture medium or reagent used in the present invention is free of any substance of non-human animal origin. In an embodiment, any culture medium and reagent used is free of serum of non-human animal origin. In an embodiment, any culture medium and reagent used is free of serum of any origin, even human.

Advantageously, the culture medium used in the present invention for cell adhesion contains human platelet lysate.

Another object of the present invention is a composition comprising thawed MSC, preferably thawed WG-MSC, as described above, for use in the treatment of sepsis.

Another object of the present invention is a pharmaceutical composition comprising, as active substances, clinical grade thawed mesenchymal stem cells from Wharton's jelly such as described above, for the use in the treatment of sepsis.

Said composition also comprises a pharmaceutically acceptable excipient.

According to the present invention, a pharmaceutically acceptable excipient is an excipient containing no substance of non-human animal origin and suitable for use in contact with the cells of human individuals, without toxicity, irritation or induced allergic response. A person skilled in the art will know how to select a pharmaceutically acceptable excipient depending on the galenic formulation of the composition and its method of administration.

By way of example, said excipient is 4% albumin or a hydroxyethyl starch solution (HEA) 130/0.42.

Said pharmaceutical composition can be in the form of an infusion product and packaged in an infusion bag.

Another object of the present invention is a medicament comprising thawed MSC, preferably thawed WG-MSC, as described above, for use in the treatment of sepsis.

In an embodiment, the MSC, preferably WG-MSC used in the invention can be administered to the patient systematically or locally.

In an embodiment, the MSC, preferably WG-MSC used in the invention, can be administered to the patient by intravenous, intravascular, intracerebral, parenteral, intraperitoneal, epidural, intra-spinal, intrastemal, intra-articular, intra-synovial, intrathecal, intra-arterial, intracardiac or intramuscular route.

In an embodiment, the MSC, preferably WG-MSC used in the invention, can be administered to the patient by bolus injection (also termed rapid injection) or by continuous infusion (also termed slow injection).

In a preferred embodiment, the clinical grade thawed WG-MSC for use in the treatment of sepsis are administered intravenously.

According to the present invention, the clinical grade thawed WG-MSC described above can be administered to a patient suffering from sepsis with a dose of about from $0.3 \times 10^6$ to $3 \times 10^6$ cells per kg of weight, in particular a dose of $1 \times 10^6$ cells per kg of weight. A person skilled in the art can adjust the dose according to the severity of the infection, the weight of the patient, the number or the frequency of administrations.

In an embodiment, the MSC, preferably WG-MSC, used in the invention, can be administered to the patient at a dose ranging from $10^3$ to $10^9$ MSC/kg, preferably from $10^4$ to $10^8$ MSC/kg, preferably from $10^5$ to $10^7$ MSC/kg.

In an embodiment, the MSC, preferably WG-MSC, used in the invention, can be administered to the patient at a dose of $1 \times 10^5$ MSC/kg, $2 \times 10^5$ MSC/kg, $3 \times 10^5$ MSC/kg, $4 \times 10^5$ MSC/kg, $5 \times 10^5$ MSC/kg, $6 \times 10^5$ MSC/kg, $7 \times 10^5$ MSC/kg, $8 \times 10^5$ MSC/kg, $9 \times 10^5$ MSC/kg, $1 \times 10^6$ MSC/kg, $2 \times 10^6$ MSC/kg, $3 \times 10^6$ MSC/kg, $4 \times 10^6$ MSC/kg, $5 \times 10^6$ MSC/kg, $6 \times 10^6$ MSC/kg, $7 \times 10^6$ MSC/kg, $8 \times 10^6$ MSC/kg, $9 \times 10^6$ MSC/kg, $1 \times 10^7$ MSC/kg.

In an embodiment, the MSC, preferably WG-MSC, used in the invention, can be administered to the patient at a dose ranging from $10^3$ to $10^9$ MSC/kg/day, preferably from $10^4$ to $10^8$ MSC/kg/day, preferably from $10^5$ to $10^7$ MSC/kg/day.

In an embodiment, the MSC, preferably WG-MSC, used in the invention, can be administered to the patient at a dose of $1 \times 10^5$ MSC/kg/day, $2 \times 10^5$ MSC/kg/day, $3 \times 10^5$ MSC/kg/day, $4 \times 10^5$ MSC/kg/day, $5 \times 10^5$ MSC/kg/day, $6 \times 10^5$ MSC/kg/clay, $7 \times 10^5$ MSC/kg/day, $8 \times 10^5$ MSC/kg/day, $9 \times 10^5$ MSC/kg/day, $1 \times 10^6$ MSC/kg/day, $2 \times 10^6$ MSC/kg/day, $3 \times 10^6$ MSC/kg/day, $4 \times 10^6$ MSC/kg/day, $5 \times 10^6$ MSC/kg/day, $6 \times 10^6$ MSC/kg/day, $7 \times 10^6$ MSC/kg/day, $8 \times 10^6$ MSC/kg/day, $9 \times 10^6$ MSC/kg/day, $1 \times 10^7$ MSC/kg/day.

In an embodiment, the MSC, preferably WG-MSC, used in the invention, can be administered to the patient at a dose ranging from $10^3$ to $10^9$ MSC/day, preferably from $10^4$ to $10^8$ MSC/day, preferably from $10^5$ to $10^7$ MSC/day.

In an embodiment, the MSC, preferably WG-MSC, used in the invention, can be administered to the patient at a dose of $1 \times 10^5$ MSC/kg/day, $2 \times 10^5$ MSC/day, $3 \times 10^5$ MSC/day, $4 \times 10^5$ MSC/day, $5 \times 10^5$ MSC/day, $6 \times 10^5$ MSC/day, $7 \times 10^5$ MSC/day, $8 \times 10^5$ MSC/day, $9 \times 10^5$ MSC/day, $1 \times 10^6$ MSC/day, $2 \times 10^6$ MSC/day, $3 \times 10^6$ MSC/day, $4 \times 10^6$ MSC/day, $5 \times 10^6$ MSC/day, $6 \times 10^6$ MSC/day, $7 \times 10^6$ MSC/day, $8 \times 10^6$ MSC/day, $9 \times 10^6$ MSC/day, $1 \times 10^7$ MSC/day.

In an embodiment, the MSC, preferably WG-MSC, used in the invention, can be administered in a single dose, or in multiple doses spaced over time.

In an embodiment, the MSC, preferably WG-MSC, used in the invention, can be administered once per day, twice per day, three times par day or more.

In an embodiment, the MSC, preferably WG-MSC, used in the invention, can be administered every day, every two days, every three days, every four days, every five days, every six days.

In an embodiment, the MSC, preferably WG-MSC, used in the invention, can be administered once per week, every week, every two weeks, every three weeks.

In an embodiment, the MSC, preferably WG-MSC, used in the invention, can be administered once per month, every month, every two months, every three months, every four months, every five months, every six months or more.

According to the invention, the thawed WG-MSC described above can be diluted before use in a suitable excipient, for example a 4% albumin solution (4 g/100 mL) or a hydroxyethyl starch solution (HEA) 130/0.42.

The thawed WG-MSC for the treatment of sepsis according to the present invention can be used alone or before, during or after another sepsis treatment, in particular an antibiotic treatment.

In an embodiment, the sepsis treatments are well known to a person skilled in the art, and include, but are not limited to, antibiotic therapy, antifungal therapy, vascular filling, administration of vasopressor agents, and corticotherapy.

In an advantageous embodiment, the clinical grade thawed WG-MSC for use in the treatment of sepsis are administered to patients suffering from sepsis under antibiotic treatment.

In an embodiment, the patient is being treated with at least one antibiotic. In an embodiment, the patient is being treated with at least two antibiotics. In an embodiment, the patient is being treated with at least three antibiotics or more.

Examples of antibiotics for the treatment of sepsis include, but are not limited to, ampicillin, azithromycin, aztreonam, cefazolin, cefepime, clindamycin, levofloxacin, linezolid, meropenem, metronidazole, piperacillin, tazobactam, tobramycin and vancomycin.

In an embodiment, the clinical grade thawed WG-MSC for use in the treatment of sepsis are administered to patients suffering from sepsis under antifungal treatment.

In an embodiment, the patient is being treated with at least one antifungal. In an embodiment, the patient is being treated with at least two antifungals. In an embodiment, the patient is being treated with at least three antifungals or more.

Examples of antifungals for the treatment of sepsis include, but are not limited to, amphotericin B deoxycholate, anidulafungin, caspofungin, fluconazole, itraconazole, micafungin and voriconazole.

In an embodiment, the clinical grade thawed WG-MSC for use in the treatment of sepsis are administered to patients suffering from sepsis under vascular filling.

Vascular filling makes it possible to correct hypovolemia, to maintain mean arterial pressure at greater than 65 mmHg and to limit the clinical signs of hypoperfusion, by restoring the intravascular volume. Vascular filling is carried out by means of solutes.

Examples of solutes for vascular filling in the treatment of sepsis include, but are not limited to, colloids and crystalloids.

In an embodiment, the clinical grade thawed WG-MSC for use in the treatment of sepsis are administered to patients suffering from sepsis under treatment with vasopressor agents.

In an embodiment, the patient is being treated with at least one vasopressor agent. In an embodiment, the patient is being treated with at least two vasopressor agents. In an embodiment, the patient is being treated with at least three vasopressor agents or more.

Examples of vasopressor agents for the treatment of sepsis include, but are not limited to, catecholamines (including, noradrenaline and adrenaline) and vasopressin.

In an embodiment, the clinical grade thawed WG-MSC for use in the treatment of sepsis are administered to patients suffering from sepsis under corticoid treatment.

In an embodiment, the patient is being treated with at least one corticoid. In an embodiment, the patient is being treated with at least two corticoids. In an embodiment, the patient is being treated with at least three corticoids or more.

Examples of corticoids for the treatment of sepsis include, but are not limited to, cortisone, hydrocortisone and prednisone.

Other treatments are suitable for sepsis and are well known to a person skilled in the art.

Examples of such treatments include, but are not limited to, AB103, recombinant alkaline phosphatase recAP, CaCP29, activated drotrecogin alfa, EA-230, eritoran, esmolol, GM-CSF, IFNγ, lenercept, levosimendan, LR12, selepressin, talactoferrin alpha and human recombinant thrombomodulin.

Another aspect of the invention relates to a method for preparing clinical grade mesenchymal stem cells from Wharton's jelly. The method of the invention aims to produce WG-MSC having a better proliferation capacity.

In an embodiment, the method of the invention aims to produce WG-MSC as defined in the present invention. In an embodiment, the method of the invention aims to produce WG-MSC as defined in the present invention for use in the treatment of sepsis.

Said method comprises the following steps:
(i) cultivating a human umbilical cord tissue containing Wharton's jelly for cell adhesion;
(ii) incubating the adherent cells obtained at step (i) in a medium containing platelet lysate.

Said method comprises the following steps:
(i) cultivating a human umbilical cord tissue containing Wharton's jelly in a culture medium for cell adhesion;
(ii) incubating the adherent cells obtained at step (i) in a medium containing platelet lysate.

In an embodiment, said method comprises the following steps:
cultivating a human umbilical cord tissue containing Wharton's jelly in a clinical grade culture medium for cell adhesion;
(ii) incubating the adherent cells obtained at step (i) in a medium containing platelet lysate;
characterised in that said tissue comes from a mother meeting at least one of the following criteria: having received an administration of oxytocin during childbirth, having given birth by directed labour, having given birth at term, not having presented pre-eclampsia during the pregnancy, whose child has not presented neonatal disorders and having been subject to an intake of tobacco smoke during the pregnancy.

The aforesaid criteria for selecting umbilical cords relating to the mother, make it possible to obtain WG-MSC with better proliferation properties.

According to the invention, the human umbilical cord tissues are collected in maternity units immediately after the delivery from a mother meeting the above criteria.

In an embodiment, the human umbilical cords are selected and cultivated. In an embodiment, the umbilical arteries and veins are removed before culture of the umbilical cords. In an embodiment, the umbilical arteries and veins are not removed before culture of the umbilical cords.

In an embodiment, the umbilical cords are washed before their culturing. In an embodiment, the umbilical cords are rinsed in a solution of α-MEM, preferably in a clinical grade α-MEM solution. In an embodiment, the α-MEM solution, preferably the clinical grade α-MEM solution, further comprises at least one antibiotic and/or at least one antifungal. In an embodiment, said at least one antibiotic is selected from gentamicin, amoxicillin and vancomycin. In an embodiment, said at least one antifungal is amphotericin B.

In an embodiment, the umbilical cords are rinsed before their culturing. In an embodiment, the umbilical cords are rinsed in a solution of PBS.

In an embodiment, the culture of human umbilical cord tissue containing Wharton's jelly for cell adhesion is a dry culture. In an embodiment, the culture medium, preferably the clinical grade culture medium, for cell adhesion used at step (i) is an α-MEM medium.

In an embodiment, the medium containing the platelet lysate used at step (ii) is an α-MEM medium. In an embodiment, the medium containing the platelet lysate used at step (ii) further comprises from 1% to 20% platelet lysate, preferably from 1% to 15%, preferably from 1% to 10%, preferably from 2.5% to 7.5%, preferably about 5% platelet lysate. In an embodiment, the medium containing the platelet lysate used at step (ii) further comprises at least one antibiotic. In an embodiment, said at least one antibiotic is gentamicin. In an embodiment, the medium containing the platelet lysate used at step (ii) further comprises heparin.

In an embodiment, step (ii) of the method according to the invention is carried out under conditions of hypoxia, preferably at about 5% $CO_2$/5% $O_2$. In an embodiment, step (ii) of the method according to the invention is carried out at 37° C.

In an embodiment, during the implementation of step (ii) of the method according to the invention, the cells are cultured up to 80%+/−10% confluence.

Advantageously, step (ii) of said method is repeated several times, in particular two or three times. In the present invention, "passage" means each repetition of step (ii) of the method. For example, the first implementation of step (ii) of the method corresponds to passage P0; its first repetition corresponds to the first passage (or passage P1); its second repetition corresponds to the second passage (or passage P2); etc.

According to the invention, when step (ii) is repeated after reaching 80%+/−10% confluence, the cells are detached by any technique known to a person skilled in the art, in particular by the action of clinical grade trypsin.

According to the invention the cells harvested at the end of step (ii) are cryopreserved at about −20° C., preferably at about −80° C., preferably between −150° C. and −196° C., preferably at about −150° C.

EXAMPLES

Example 1: Production of WG-MSC

Isolation of WG-MSC

The human umbilical cords are collected at the maternity unit of the Regional Teaching Hospital Center (Centre Hospitalier Régional Universitaire—CHRU) in Nancy after having informed the donor mothers and having obtained their written consent. The cords are placed in a collection medium and preserved at 4° C. The collection medium, placed in a sterile container (for example, Cryokits, Verreries Talangonnaises), is composed of phosphate-buffered saline (PBS, Macopharma, BC0120020) in order to ensure a pH close to 7, heparin in order to prevent the residual blood coagulating, an antibiotic (gentamicin). The cord can be kept for 24 hours at 4° C. in a transport medium after collection.

Upon receipt, the umbilical cords are immersed for one hour at ambient temperature in an antibiotic-antifungal solution composed of gentamicin, amoxicillin, vancomycin and amphotericin B in a clinical grade α-MEM culture medium (Macopharma, BC0110010) with a respective final concentration of 0.5 g/L; 1 g/L; 1 g/L and 0.05 g/L. This bath reduces the risks of microbial development during culture which would be secondary to a contamination during collection.

Once the cord is decontaminated, the vein and the outer part of the cord are washed with PBS. 10 mL of PBS are injected into the umbilical vein using a syringe in order to remove the residual blood. The cord is then pre-cut into pieces of 5 cm using a sterile scalpel and then fine transverse slices (2 to 3 mm thick) are produced. These pieces are then placed in culture dishes with removable lids (TPP, 90552). The dry adhesion of the pieces to the bottom of the dish is carried out for 15 minutes then complete medium, composed of α-MEM supplemented by 5% platelet lysate (Macopharma, BC0190020) in the presence of gentamicin and heparin, is added. The culture is carried out in a dedicated incubator at 37° C. and 5% $CO_2$ and in hypoxia (5% $O_2$). After five days, the culture medium is changed.

After about 10 days of culture, the WG-MSC will have migrated and adhered to the bottom of the culture dish. The pieces are then removed using sterile pliers and the dish is washed with PBS buffer. The cells are then cultured to confluence (>80%) for between 15 days and 3 weeks (between D14 and D21).

Culture of WG-MSC

After reaching confluence, the cells are detached by the action of recombinant trypsin GMP (TrypLE, Invitrogen).

After washing, the cells are re-seeded at $1\times10^3$ cells per $cm^2$ in passage 1 in complete medium. A culture unit with 2 stages of 1270 $cm^2$ surface area of CellSTACK type (CELL-STACK2, Macopharma) is used as well as a universal cap with chimney (MPC cap, Macopharma). The seeding kit (BC0400011, Macopharma) comprises the system of tubes enabling the application of the various components of the medium and the cells, and the connections for connecting to the culture vessel.

The medium is changed once per week until obtaining the confluence (>80%) (between D7 and D8 after the start of culture). For this, a medium changing kit (BC0400021, Macopharma), comprising the system of tubes for applying the various components of the medium, a waste bag and the connections for connecting to the culture vessel, is used, as well as a universal cap with chimney. However, most of the time, passage P1 lasts for 1 week and the change of medium is not necessary.

On obtaining the confluence, the cells are cryopreserved in a master cell bank (MCB). The Food and Drug Administration (FDA) defines an MCB as a collection of cells of uniform composition, derived from a tissue or a single cell, and stored in an aliquot under defined conditions.

Final Harvesting of Cells

After reaching confluence at the end of passage P1, the cells are harvested by the action of trypsin, as described above, and then washed. A viability check and cell count as well as the various checks of P1 are performed (see table below). The cells are then frozen.

Preservation of MSC and the MCB

The MSC are stored in tanks (in nitrogen vapour) at −150° C. with continuous monitoring of the temperature and nitrogen level. In addition, 5 to 10 sample tubes of MSC are also frozen to produce controls.

Thawing the MCB and Washing the MSC The MSC are thawed and washed using a Sepax technique (Biosafe) then re-seeded in passage 2 and then passage 3, following the same protocol as for P1.

Final Harvesting of Cells

After reaching confluence at the end of passage P3, the cells are harvested by the action of trypsin, as described above, and then washed. A viability check and cell count, as well as the various end of production checks, are performed (see table below). The cells are then frozen in a working cell bank (WCB). The Food and Drug Administration (FDA) define a WCB as a collection of cells derived from one or several aliquots of an MCB. The cells of the MCB are expanded by sub-cultures in series until the selected passage, after which the cells are combined, concentrated and aliquoted. One or several aliquots of the WCB obtained in this way can be used in order to produce a batch of the final product with a view to its use.

Preservation of the MSC of the WCB

The MSC are stored in tanks (in nitrogen vapour) at −150° C. with continuous monitoring of the temperature and nitrogen level. In addition, 5 to 10 sample tubes of MSC are also frozen to produce controls.

Thawing and Washing of MSC of the WCB and Transport of the MSC

The MSC are thawed and washed using a Sepax technique (Biosafe) and then taken up in a volume of 75 mL with 4% albumin and preserved at between 4 and 10° C. The MSC are packaged in bags (150 ml bags), labelled according to the regulatory operating mode; said bag is placed in a secondary packaging (plastic bag), itself labelled, then in a transport container with a temperature logger, a certificate of validation, an injection notice and a sheet of tolerance after administration. The transport of the MSC to the site of administration is carried out by a transporter approved by the CHRU.

Quality Controls Carried Out During the Course of the Production Process

In order to guarantee the sterility and safety of the product to be administered, product controls are carried out at each step of the culture process. All of the quality controls are listed in Table 1.

TABLE 1

| Steps | Controls carried out at each step |
| --- | --- |
| Receipt of the sample: | Infectious markers of the donor (serologies/DGV) |
| Change of medium<br>The medium is changed once per week | Sterility control |
| Trypsinisation: end of P0 | Cell count<br>Cell viability<br>Cellular phenotype<br>Sterility control<br>CFU-F |
| Trypsinisation: end of P1 MCB | Cell count<br>Cell viability<br>Cellular phenotype<br>Sterility control<br>Check for the absence of endotoxins and mycoplasms<br>CFU-F<br>Control of the differentiation into cells of the mesodermal tissue<br>Telomerase (hTERT)<br>Karyotype<br>Mixed lymphocytes culture<br>Potency test (in course of definition) |
| Trypsinisation: end of P2 | Cell count<br>Cell viability<br>Cellular phenotype<br>Sterility control<br>CFU-F |
| Final harvest: end of P3 (prefreezing)<br>After reaching confluence at the end of $P_3$, the MSC are trypsinised, washed and then frozen. | Cell count<br>Cell viability<br>Cellular phenotype<br>Sterility control<br>Check for the absence of endotoxins and mycoplasms<br>CFU-F<br>Control of the differentiation into cells of the mesodermal tissue<br>Telomerase (hTERT)<br>Karyotype<br>Mixed lymphocytes culture<br>Potency test (in course of definition) |

Cellular Controls

Cell Count

On the starting product and at each cell harvesting step (P0 and P3), the cell count is determined using a haemocytometer after lysis of red blood cells.

Cell Viability

On the starting product and at each cell harvesting step, the viability is determined by flow cytometry by 7-AAD marking at the end of P0, P1, P2, P3 should be >80%.

Cellular Phenotype

The expression of surface markers characteristic of a cell type will be determined by flow cytometry after marking cells with monoclonal antibodies or the corresponding isotype controls.

At least 60% of cells should express the following antigens: CD90, CD73, CD105, CD44 and 80% of cells should not express: CD34, CD11b, CD19, CD45, HLA-DR (and/or IMF <2 times IMF of the isotype control). The marker CD106 should be identified on at least 10% of the cells.

CFU-F

The clonogenic capacity will be measured by the culture of fibroblast progenitors (colony forming unit fibroblast: CFU-F). The CFU-F (>50 cells) are counted with an inverted microscope at ×10 magnification, after fixing with methanol and staining with Giemsa. Briefly, 2.5 and $5 \times 10^2$ cells are seeded in 5 mL of the medium in a 25 cm² flask. The medium is entirely renewed twice per week. The culture is stopped at D10 and is fixed and stained with Giemsa. The colonies of more than 50 cells are then counted. The culture of CFU-F is carried out at the end of each passage.

Immunological Control

The absence of immunostimulant capacity of the MSC is controlled. To do this, a mixed lymphocyte culture will be realised using the produced and irradiated MSC as stimulant cells, and mononuclear cells of two healthy controls. The immunostimulant is evaluated by measurement of the stimulation index. These tests are carried out in the quality control sector of the "punctually prepared innovative therapy drugs" department (Département "Médicaments de Thérapie Innovante Préparés Ponctuellement-MTI-PP) of the cell therapy and tissue bank unit (Unité de Thérapie Cellulaire et banque de Tissus-UTCT) of Nancy. The immunomodulatory effect is evaluated by adding MSC as a third partner to a conventional mixed lymphocyte culture.

Microbiological Control

Control of Infectious Markers of the Donor

A viral genome diagnosis is carried out with the donor for HIV, HBV and HCV. Compliant infectious markers are: HIV: Combined test P24 Ag+anti-HIV Ab 1+2: Negative, HIV PCR: Negative, HBV: HBs Ag negative, anti HBc Ab negative, HBV PCR: Negative, HCV: Anti-HCV Ab: Negative, HCV PCR: Negative, HTLV: Anti-HTLV Ab I+II: Negative, Syphilis: Anti-TP Ab: Negative, CMV, EBV and Toxoplasmosis: negative IgM, negative or positive IgG.

Bacteriology

The microbiological control is carried out according to the recommendations of the French agency for the safety of medicine and health products (Agence nationale de sécurité du médicament et des produits de santé-ANSM) for cellular therapy products (CTP) from aerobic and anaerobic blood cultures produced by the Bactec technique. This control is carried out at each culture step. On the thawed MSC, the results of the controls obtained after the injection of MSC in the patient must be negative. In the event of a positive microbiological control after re-injection, the clinician will be informed immediately, the identification of the microorganism will be communicated together with the results of the antibiogram in compliance with the internal procedures to the MTI-PP department.

Other Controls

Absence of hTERT Transcripts

The absence of telomerase activity is sought by qRT-PCR in the MSC after culture (end of P1 and P3). This control will be carried out on a cryopreserved aliquot of $10^6$ MSC.

Karyotype

This is carried out on a fresh cell sample of MSC obtained at the end of culture (end of P1 and P3), before cryopreservation.

Dosage of Endotoxins and Mycoplasms

This is carried out on a fresh or frozen cell sample of MSC obtained at the end of culture (end of P1 and P3), before cryopreservation.

Administration of MSC

The cells prepared in this way are administered to hospitalised patients in resuscitation presenting a septic shock or a sepsis, at a dose of at least $1\times10^6$/kg heterologous MSC in 75 mL of 4% albumin, NaCl, ACD, infused for 30 minutes by central venous route. The treatment is received and administered via central venous route, preferably in the 10 hours following the step of thawing and washing of the MSC of the WCB, and at most up to 24 hours following the step of thawing and washing of the MSC of the WCB.

Murine Model of Septic Shock

A septic shock was induced in immunocompetent C57BL/6 mice by caecal ligation and puncture (CLP). This model, which is considered as the best standard for murine septic shock, is able to mimic a human peritonitis.

After surgery, the mice were randomised in 3 groups: a group receiving $0.25\times10^6$ human WG-MSC, a group receiving $0.25\times10^6$ BM-MSC obtained by culture from a harvesting of bone marrow from a healthy donor having given his/her consent and a control group receiving PBS. The administration of MSC as well as the PBS was carried out 24 hours after the start of the septic shock, intravenously in the retro-orbital sinus.

The WG-MSC and BM-MSC are used just after thawing, without prior reculturing.

Example 2: Effect of WG-MSC on Septic Shock in Mice

Impact of WG-MSC on bacteraemia
Protocol Thawed human WG-MSC are used.

Forty-eight hours after the start of septic shock, or 24 hours after the administration of MSC, the mice were euthanised by lethal anaesthetic injection. The spleen and the blood of the mice were harvested and then seeded in order to count the number of colony forming units (CFU).

The comparison of the different groups was performed using a Kruskal-Wallis test.

Results

Two days after the septic shock, only the mice treated by WG-MSC have shown a significant reduction in the bacteraemia and the number of spleen CFU. The average number of CFU per milligram of spleen or of blood was counted. Forty-eight hours after the CLP procedure, the group treated with WG-MSC showed on average $2.3\times10^3$ CFU in aerobic condition per mg of spleen and $5.8.10^3$ CFU in anaerobic condition per mg of spleen, while the control group and the group treated with BM-MSC had an average number of CFU in aerobic condition per mg of spleen respectively of $9.5\lambda10^4$ and $5.5\times10^3$ and an average number of CFU in anaerobic condition per mg of spleen respectively of $1.3\times10^5$ and $1.1\times10^4$ (FIGS. 1A and 1B).

Figure 2:
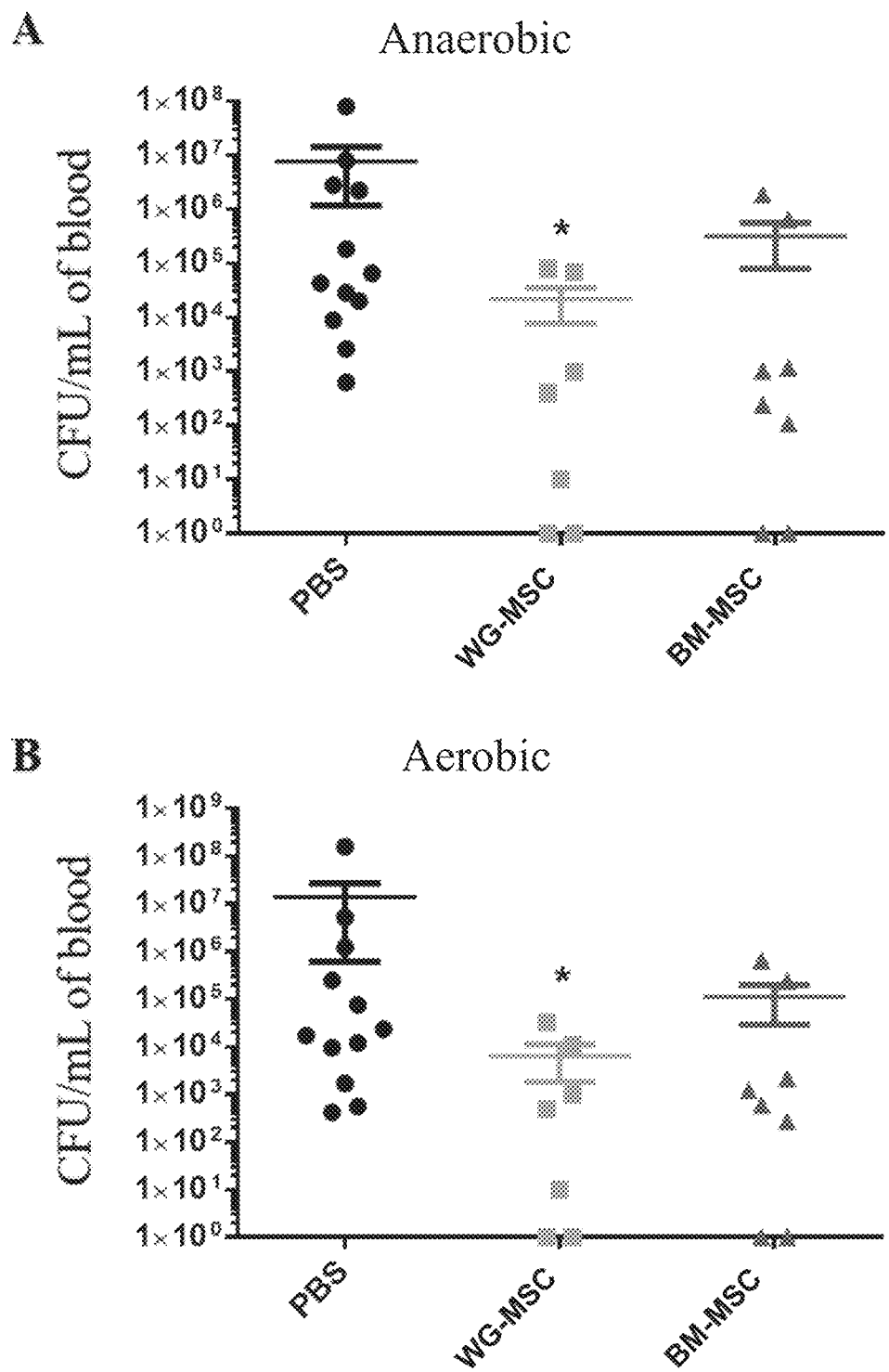
FIGS. 2A and B: these figures show, respectively, the number of CFU in anaerobic condition (A) or in aerobic condition (B) per mL of blood. The results are shown as mean±SEM. n=7-12 mice per group. *$p<0.05$ MSC versus PBS.

The results obtained in the blood are similar (FIGS. 2A and 2B). The group treated with the MSC from Wharton's jelly showed on average $6\times10^3$ CFU in aerobic condition/mL of blood and $2.1\times10^4$ CFU in anaerobic condition/mL of blood, whereas the control group and the group treated with BM-MSC had an average number of CFU in aerobic condition per mL of blood respectively of $1.3\times10^7$ and $1.1\times10^5$ and an average number of CFU in anaerobic condition per mL of blood respectively of $7.7\times10^6$ and $3.2\times10^5$.

CONCLUSIONS

These results show, for the first time, an antibacterial action of MSC from Wharton's jelly against septic shock, when they are used just after thawing.

Impact of the WG-MSC on Cell Influx within Organs
Protocol

Forty-eight hours or 7 days after the inducing of the septic shock, the mice were euthanised by intraperitoneal injection of pentobarbital and the organs were harvested. The spleen and the liver were ground then filtered. The bone marrow was extracted from the femur by rapidly injecting 1 mL of PBS into the medullary cavity. The lungs were cut into fine pieces and then placed in 2 mL of collagenase for 45 minutes before being ground and filtered. The cells extracted from the various organs were washed by centrifugation. A cell count was performed.

The cells were marked with 5 µL of anti CD45, CD11b, Ly6C, and Ly6G antibodies in order to identify and quantify, within the various organs, the total monocytes, the inflammatory and anti-inflammatory monocytes, as well as the neutrophiles.

The same protocol was carried out on healthy mice before inducing septic shock.

The comparison of the various groups was performed by a 2-way ANOVA test followed by a Tukey test. Statistical significance was accepted for $p<0.05$.

Results

Figure 3:
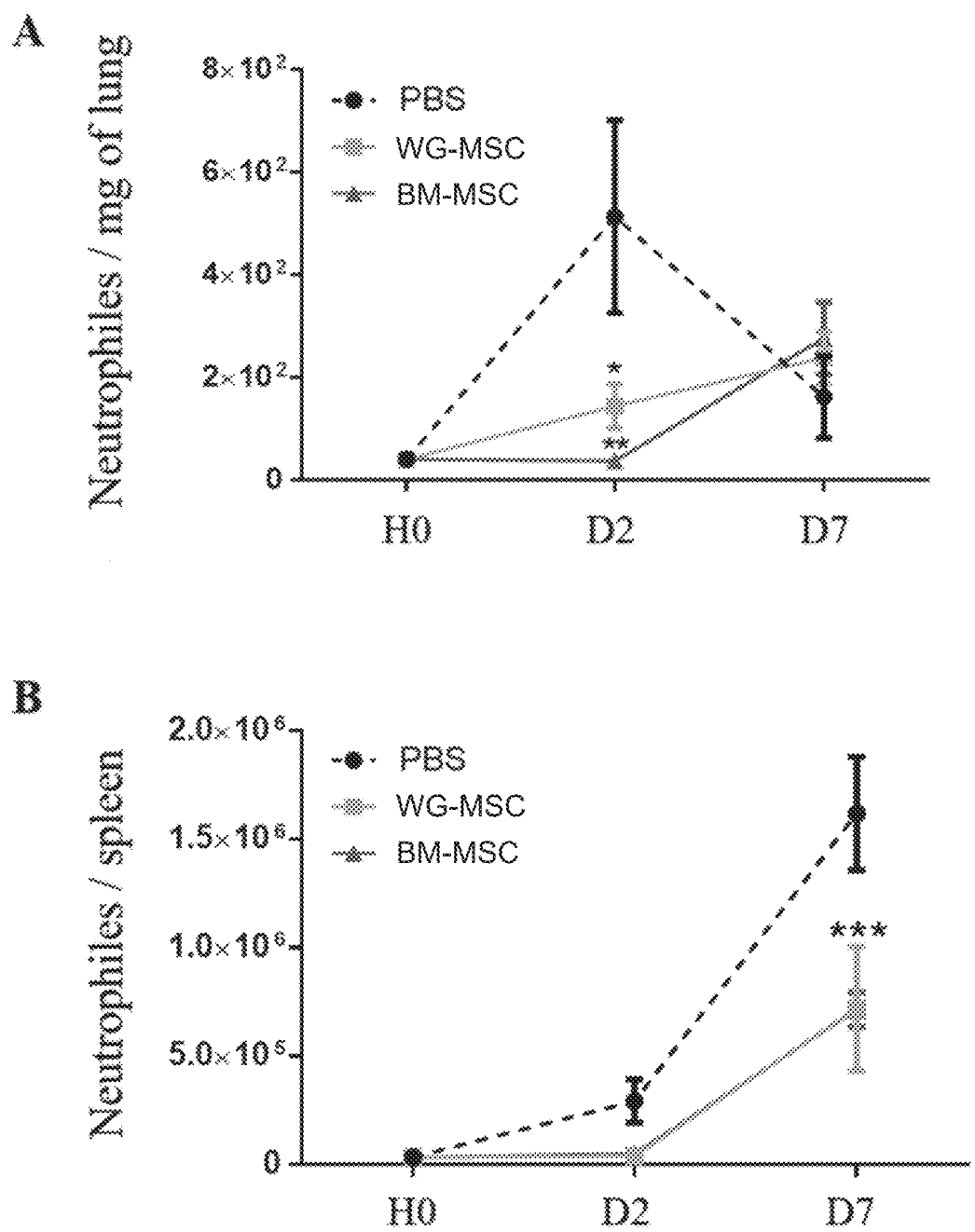
FIGS. 3A, B, C, D: these figures show, respectively, the kinetics of neutrophiles in the lung (A), spleen (B), liver (C) and femur (D). The results are shown as mean±SEM. n=4-6 mice per group. *$p<0.05$ MSC versus PBS; $p<0.01$ MSC versus PBS; *$p<0.001$ MSC versus PBS.
Figure 3:
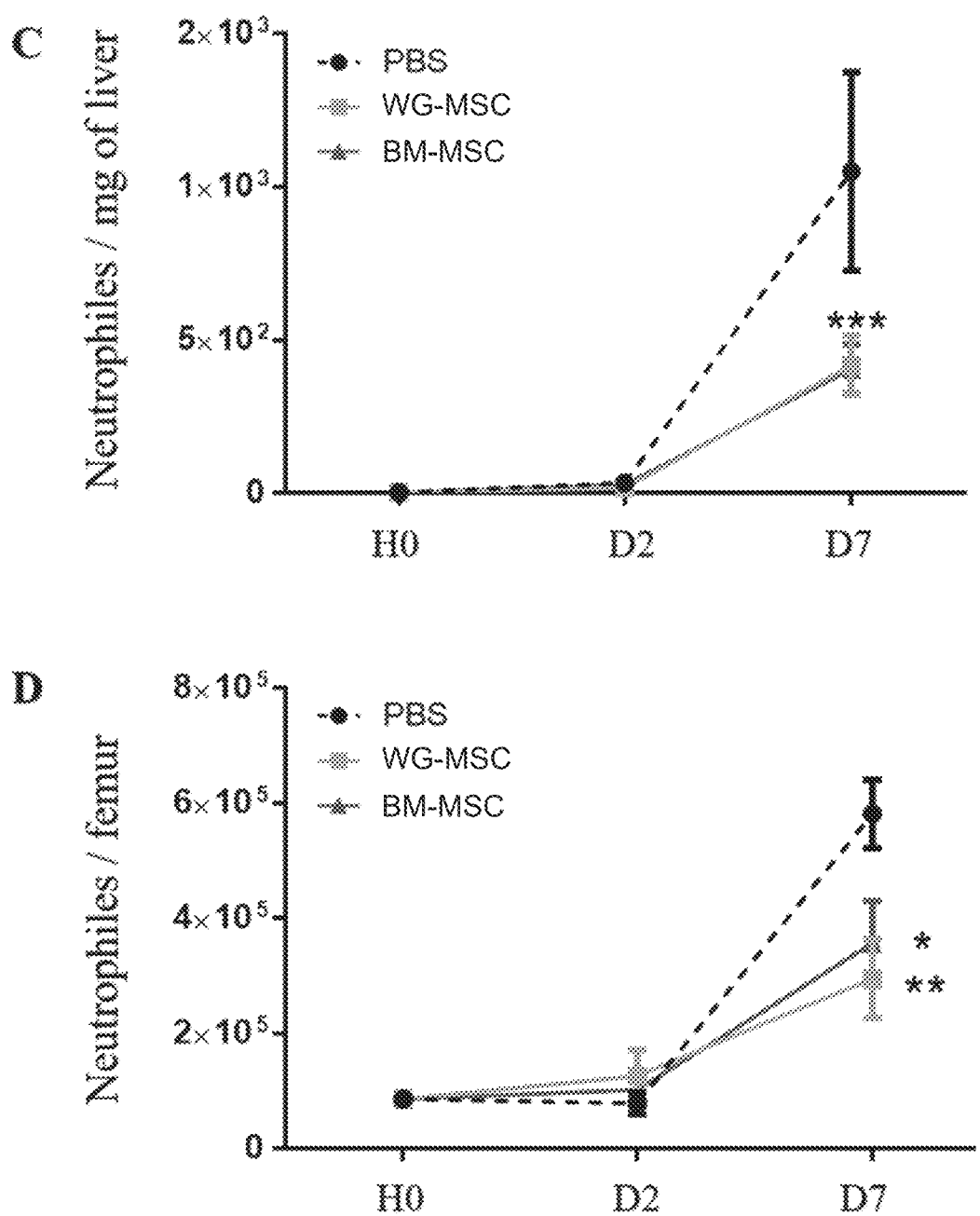

Two days after inducing the septic shock, the control mice having intravenously received a saline solution showed a significantly larger number of pulmonary neutrophiles than the mice treated by injection of MSC (FIG. 3A). At D7, a significantly smaller accumulation of neutrophiles was noted in the spleens and livers of mice treated by BM-MSC and WG-MSC ($p<0.001$) (FIGS. 3B and 3C). Seven days after CLP, the number of neutrophiles contained in the femurs of treated animals was significantly smaller compared to the control group (PBS vs. BM $p<0.05$; PBS vs. WG $p<0.01$) (FIG. 3D).

Figure 4:
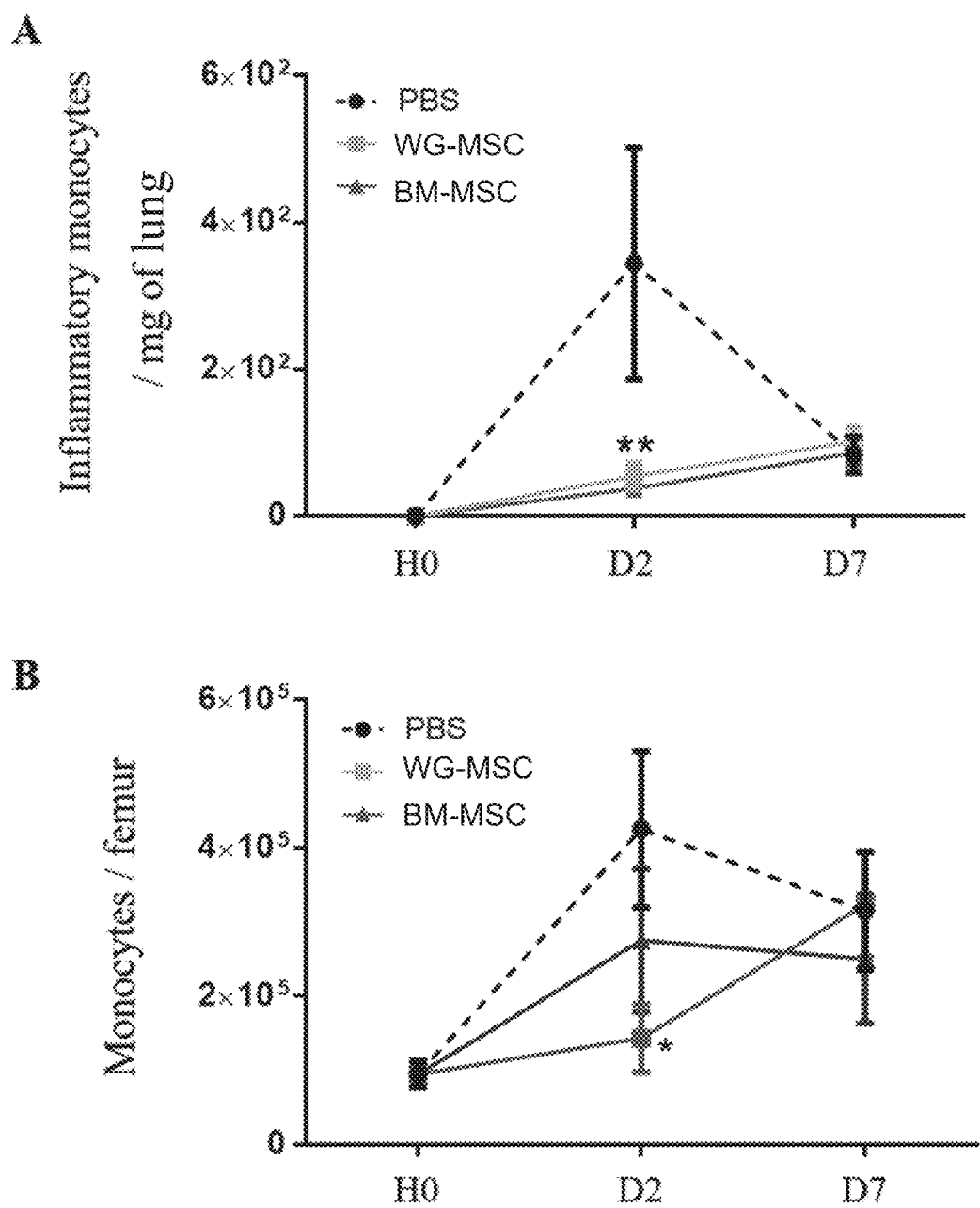
FIGS. 4A, B, C, D: these figures show, respectively, the kinetics of monocytes in the lung (A) and femur (B), or of inflammatory monocytes in the femur (C) and spleen (D). The results are shown as mean±SEM. n=4-6 mice per group. *$p<0.05$ MSC versus PBS; **$p<0.01$ MSC versus PBS; ##$p<0.01$ BM-MSC versus WG-MSC.
Figure 4:
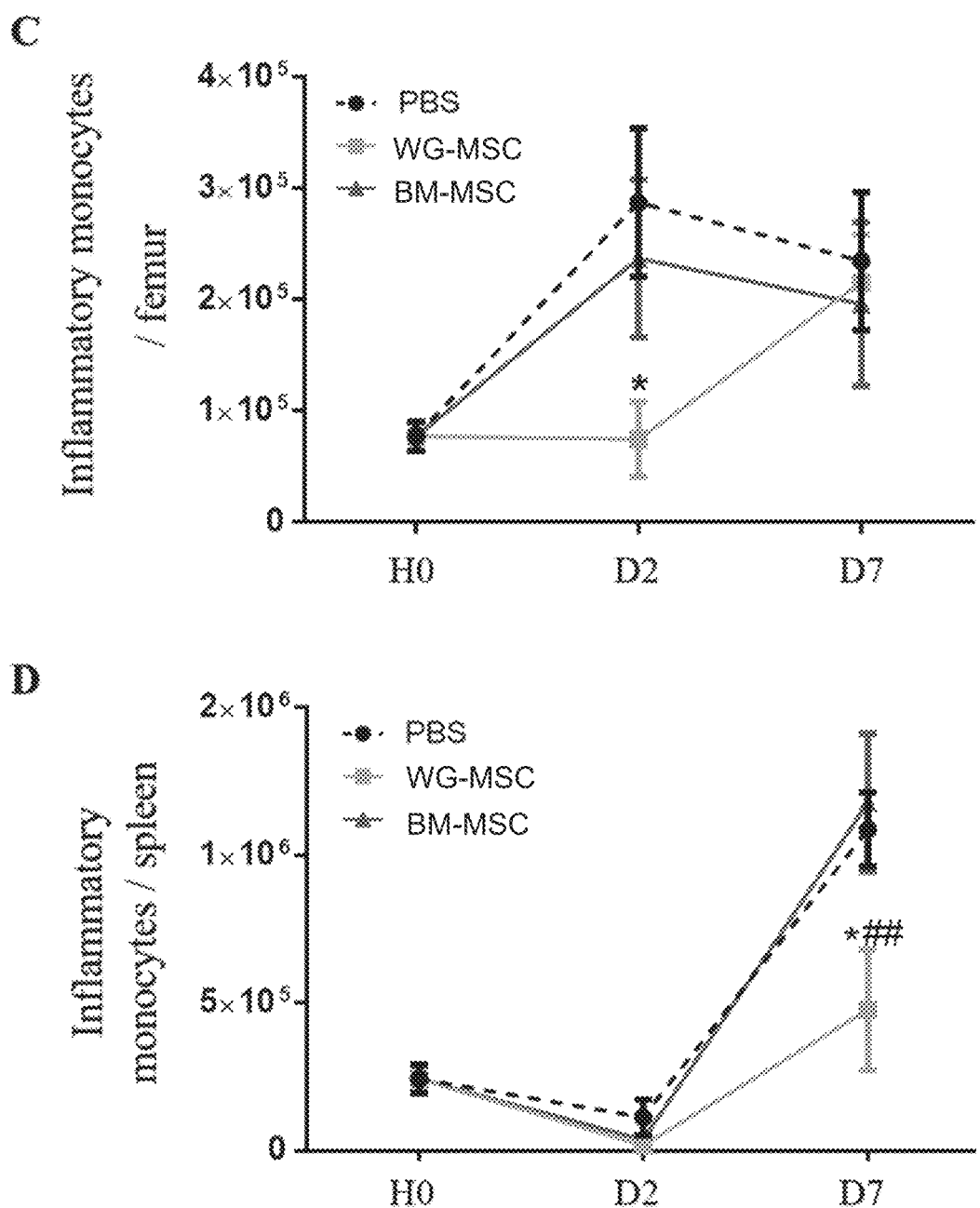

Two days after inducing the septic shock and 24 hours after injecting the MSC, the lungs of mice having received BM-MSC or WG-MSC contained a significantly smaller number of inflammatory monocytes ly6C$_{high}$ than for the control mice (p<0.01) (FIG. 4A). A significant reduction in the total number of monocytes (FIG. 4B) and in the number of inflammatory monocytes ly6C$^{high}$ (FIG. 4C) at D2 was also found in the femurs of mice treated by WG-MSC (p<0.05) when compared with the control mice, whereas no significant difference was observed between the control group and the BM-MSC group.

Seven days after inducing the septic shock, a significantly smaller number of inflammatory monocytes ly6C$^{high}$ was observed in the spleens of mice treated by WG-MSC compared to mice treated by BM-MSC (p<0.01) and by PBS (<0.05) (FIG. 4D).

This study reveals that MSC are capable of modulating the leukocyte infiltrate in a polymicrobial sepsis model. It is shown that the action of thawed WG-MSC is not limited to the first 48 hours following their injection, but that they are capable of having much later effects on cell recruitment during septic shock.

In addition to being effective at a later time, the MSC also have an early action on leukocyte traffic. In the results analysed above, it is demonstrated that, 48 hours after inducing the septic shock, the MSC decrease the influx of neutrophiles into the lungs.

These results show that WG-MSC, like BM-MSC, are capable of reducing, within the organs, the accumulation of neutrophiles involved in the development of organ failure associated with septic shock. Indeed, it is known that the abnormal accumulation of neutrophiles can induice both a vascular occlusion leading to a hypoxaemia and a tissue hypoperfusion, as well as causing dysfunctions of the microcirculation by massive release of oxygen-reactive species.

Furthermore, unlike BM-MSC, the WG-MSC have the ability to reduce both the femoral production of total monocytes two days after the septic shock, as well as the production of pro-inflammatory monocytes leading to a lesser accumulation of this monocyte subpopulation in the spleen of mice. Given that septic shock modifies the properties of the monocytes by inducing, in particular, an increase in their production of oxygen-reactive species contributing to an increase in the SOFA score (sepsis related organ failure assessment) (Martins et al., 2008), the reduction in the accumulation and production of total and pro-inflammatory monocytes induced by the injection of WG-MSC, can lead to a real benefit in the treatment of septic shock Impact of WG-MSC on Survival Protocol After inducing septic shock in C57B1/6 mice by CLP technique, 150 µL of NaCl were administered subcutaneously in order to enable vascular filling after surgery. With the aim of being as close as possible to clinical conditions, all of the mice received a dose of 50 µg/g of body weight of imipenem every 12 hours, intraperitoneally (Alcayaga-Miranda et al., 2015).

A Wilcoxon test was performed. A significant difference was acknowledged for p<0.05.

Results

Figure 5:
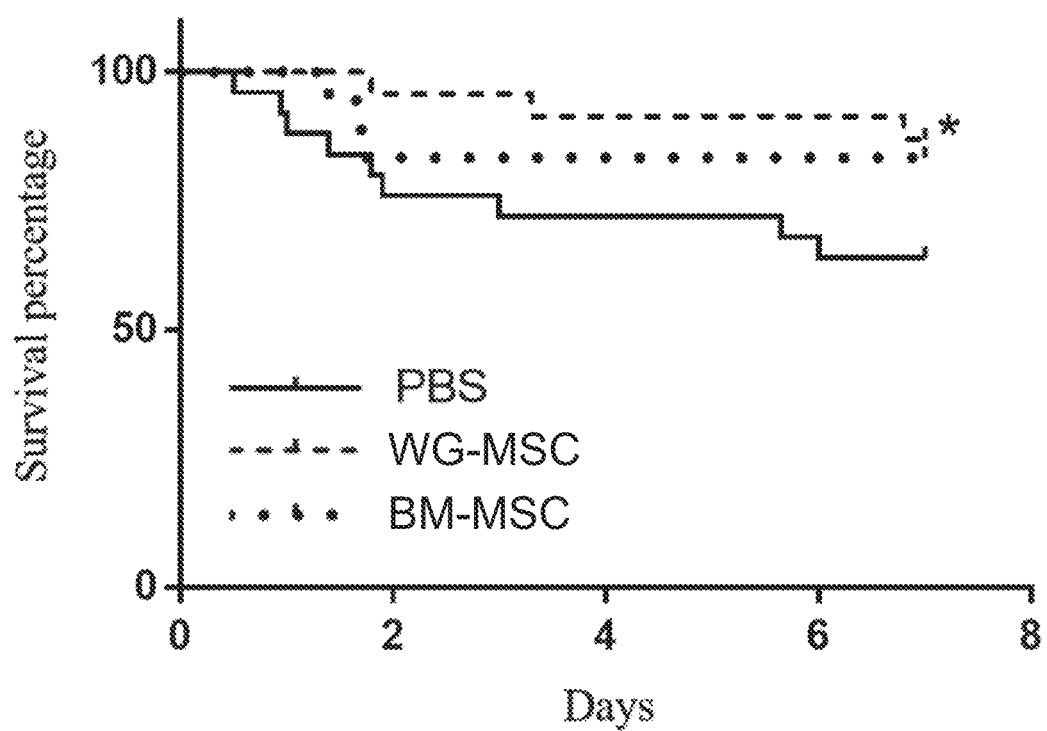
FIG. 5: this figure shows the survival rate after caecal ligation and puncture of mice treated with WG-MSC, BM-MSC, and untreated mice. The results are shown as Kaplan-Meier curves. n=18-25 mice per group. *$p<0.05$ MSC versus PBS.

The survival rate increased in mice treated by MSC compared to the control mice. A survival rate of 64% is found in the control animals, whereas 83% of the animals treated with BM-MSC and 87% treated with WG-MSC survived (FIG. 5).

The WG-MSC have a better result in terms of survival in septic shock compared with BM-MSC.

Example 3: Study of the Impact of WG-MSC on Sepsis

The effectiveness of clinical grade thawed WG-MSC produced according to the method described in parts 1.1-1.6 above, is analysed in the pig, which is the closest animal to man from the cardiovascular point of view.

Four hours after introducing a peritonitis in the pig, a dose of WG-MSC of 1×10$^6$/kg was injected intravenously. The WG-MSC were produced in clinical grade and were used just after thawing. The study, carried out over 24 hours following induction of the peritonitis, was performed as a double-blind study and in the presence of an experienced resuscitation physician. Consequently, the support was identical to that of a patient, with maintenance of the volemia and of the mean arterial pressure (>85 mmHg) by vascular filling and by noradrenaline (maximum 10 µg/kg/min) and maintenance of an adequate cardiac flow (>21/min/m$^2$) by dobutamine (maximum 20 µg/kg/min).

Figure 6:
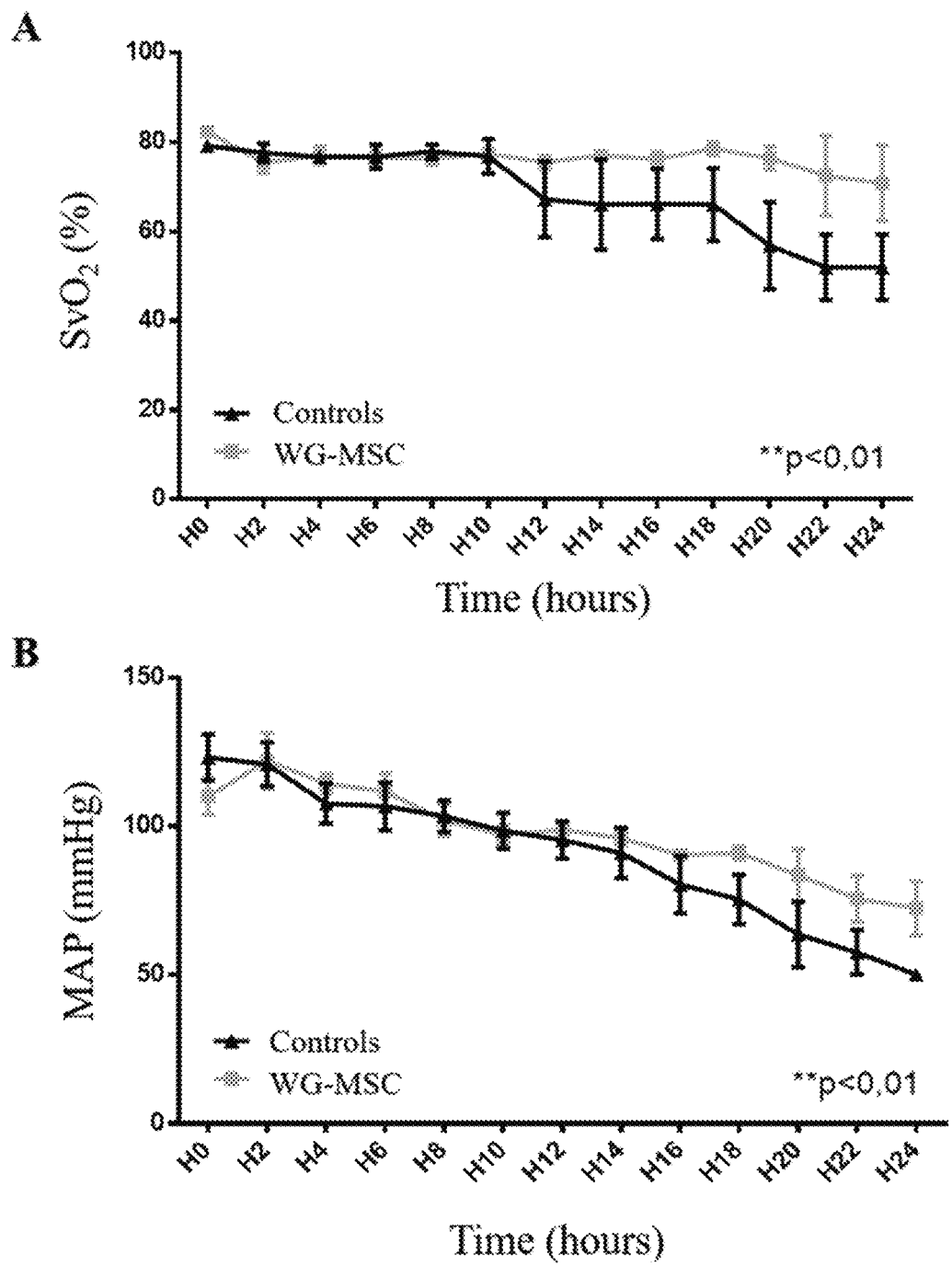
FIGS. 6A, B, C, D, E, F, G, H: these figures show the impact of the treatment by WG-MSC on sepsis in pigs compared to pigs without treatment. (A) compares the venous saturation with oxygen as a function of time, in the group with WG-MSC treatment and in the group without treatment ($p<0.01$ WG-MSC versus control). (B) compares the reduction in mean arterial pressure as a function of time, in the group with WG-MSC treatment and in the group without treatment ($p<0.01$ WG-MSC versus control). (C) compares the administered noradrenaline concentration as a function of time, in the group with WG-MSC treatment and in the group without treatment ($p<0.0001$ WG-MSC versus control). (D) compares the plasma creatinine concentration as a function of time, in the group with WG-MSC treatment and in the group without treatment ($p<0.01$ WG-MSC versus control). (E) compares the diuresis in the group with WG-MSC treatment and in the group without treatment. (F) compares the lactatemia as a function of time, in the group with WG-MSC treatment and in the group without treatment (**$p<0.01$ WG-MSC versus control). (G) compares the PaO2/FiO2 ratio as a function of time, in the group with WG-MSC treatment and in the group without treatment (*$p<0.5$ WG-MSC versus control). (H) compares the survival of animals as a function of time, in the group with WG-MSC treatment and in the group without treatment.
Figure 6:
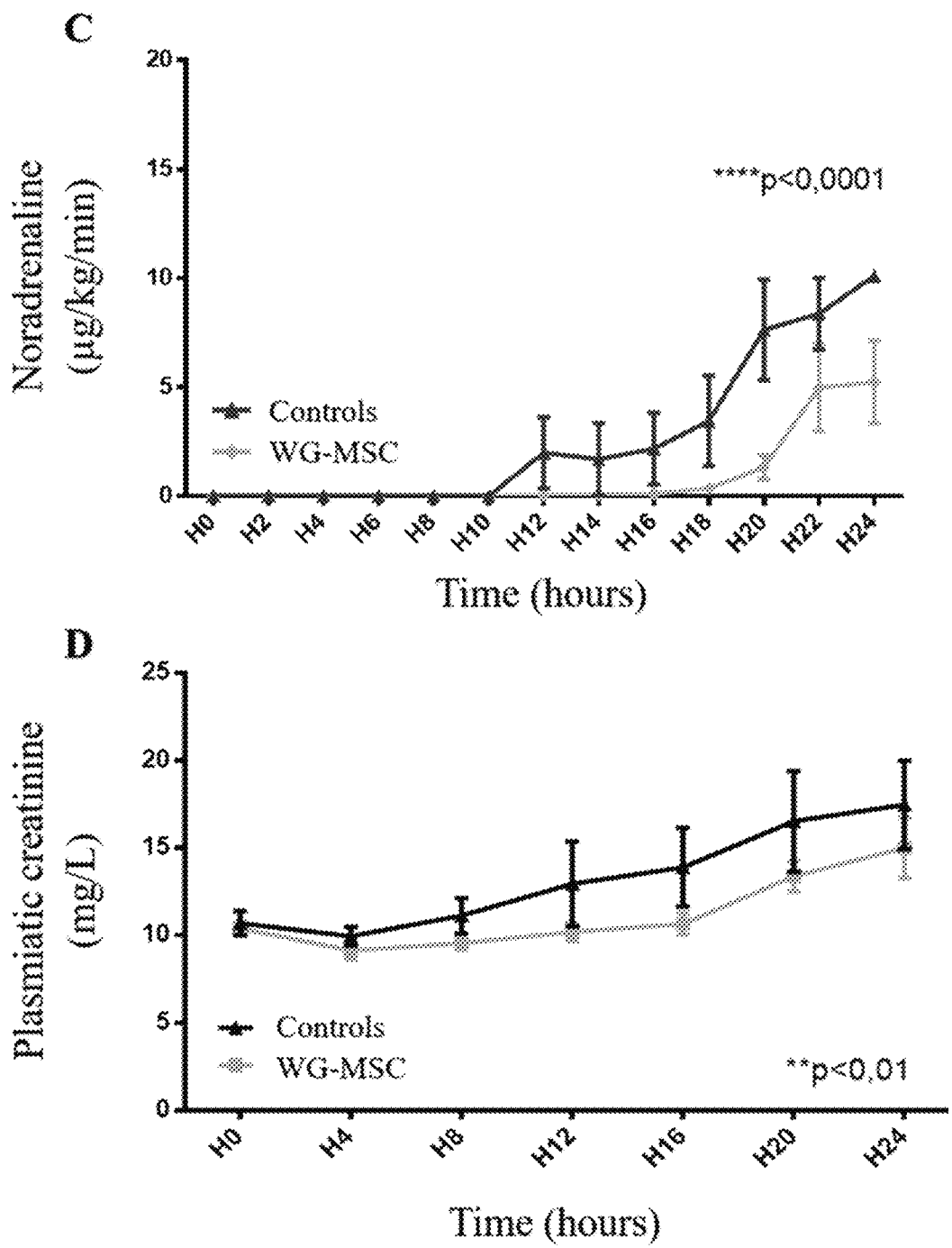
Figure 6:
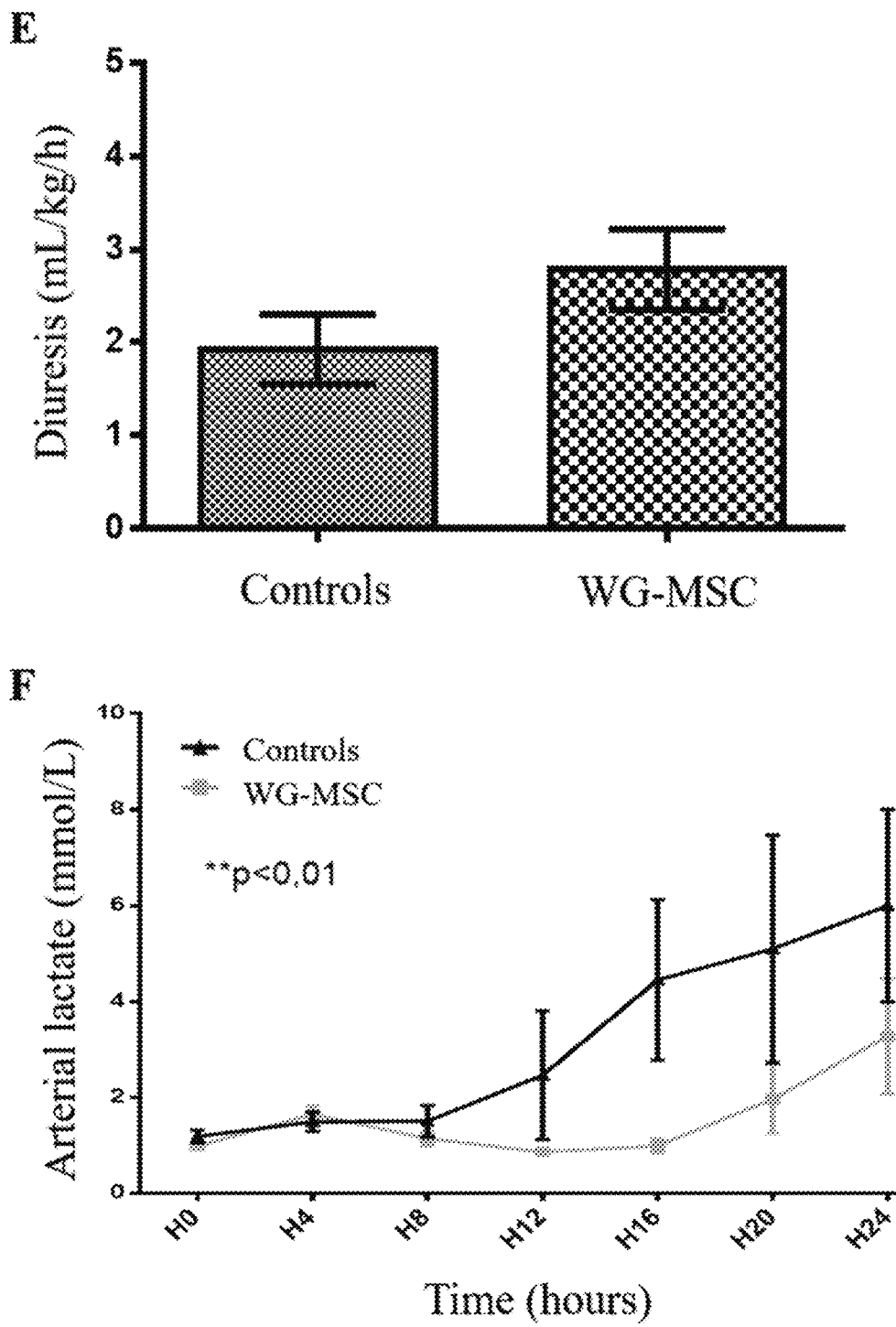
Figure 6:
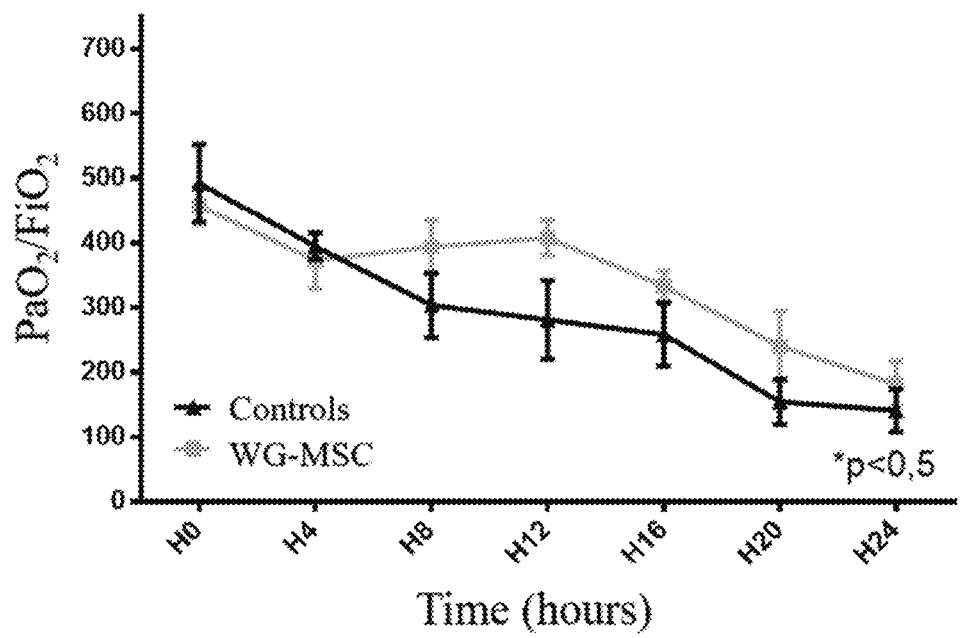
Figure 6:
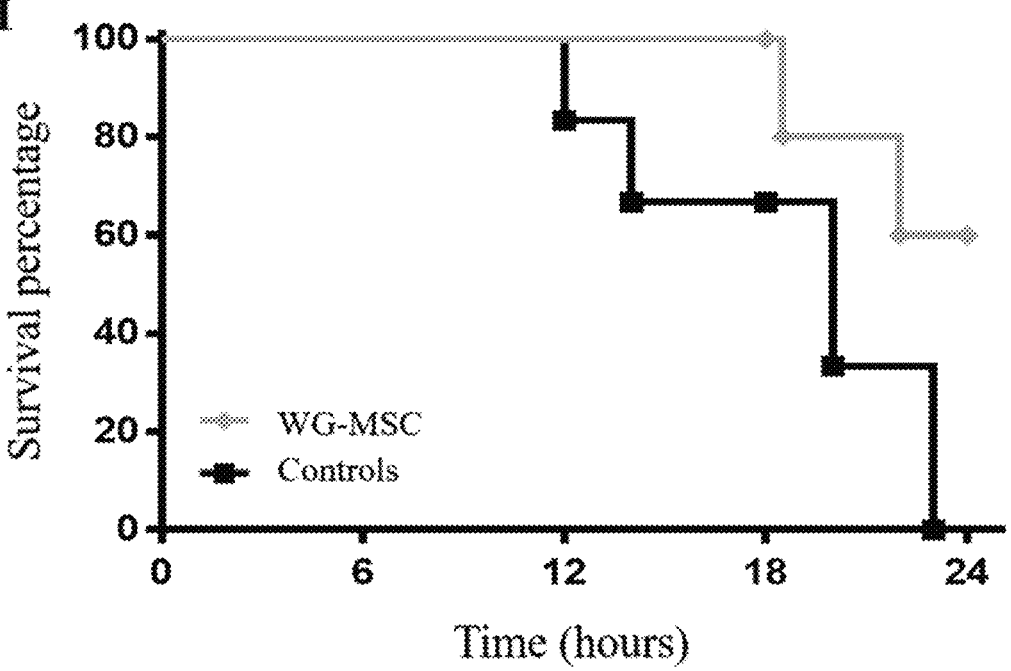

This study showed that the administration of WG-MSC significantly improved the venous saturation in oxygen, thereby demonstrating a better match between the intake of O$_2$ and the consumption of O$_2$ in the treated animals (FIG. 6A).

The administration of WG-MSC improves the cardiovascular functions as evidenced by the improvement in mean arterial pressure (MAP) in the treated animals and the later administration of noradrenaline (FIGS. 6B, 6C). The administration of WG-MSC improves renal function: the treated animals have shown a smaller increase in creatinine and a larger diuresis (FIGS. 6D, 6E).

Furthermore, the intravenous injection of WG-MSC significantly reduces lactataemia, the production of which being greater than 2 mmol/L testifies to tissue hypoxia (FIG. 6F).

The intravenous injection of WG-MSC also increases the PaO$_2$/FiO$_2$ ratio, which reflects the intensity of acute respiratory distress syndrome (FIG. 6G). Its increase in treated animals testifies to a lesser pulmonary failure than in untreated animals.

It is observed in this experiment that the increase in survival of the treated animals with respect to the untreated animals is of about 60% (FIG. 6H).

Example 4: Analysis of the Obstetric Factors

Fifty umbilical cords have been analysed by associating different obstetric parameters. The WG-MSC are isolated from these tissues according to the method described in parts 1.1-6 above.

After the extraction of data, the 27 obstetric factors (14 relating to the mother, 6 to the newborn and 7 to the labour) are analysed for correlations between these obstetric parameters and 8 biological indicators of cell proliferation (population doubling). Each variable was subjected to a bivariate linear regression (BLR). Only the factors having a significant association at a threshold of 0.15 in BLR were candidates for an analysis by multivariate linear regression (MLR). The stepwise method for selecting variables was used with an input threshold in the model at 0.1 an output threshold of the model at 0.05.

Figure 7:
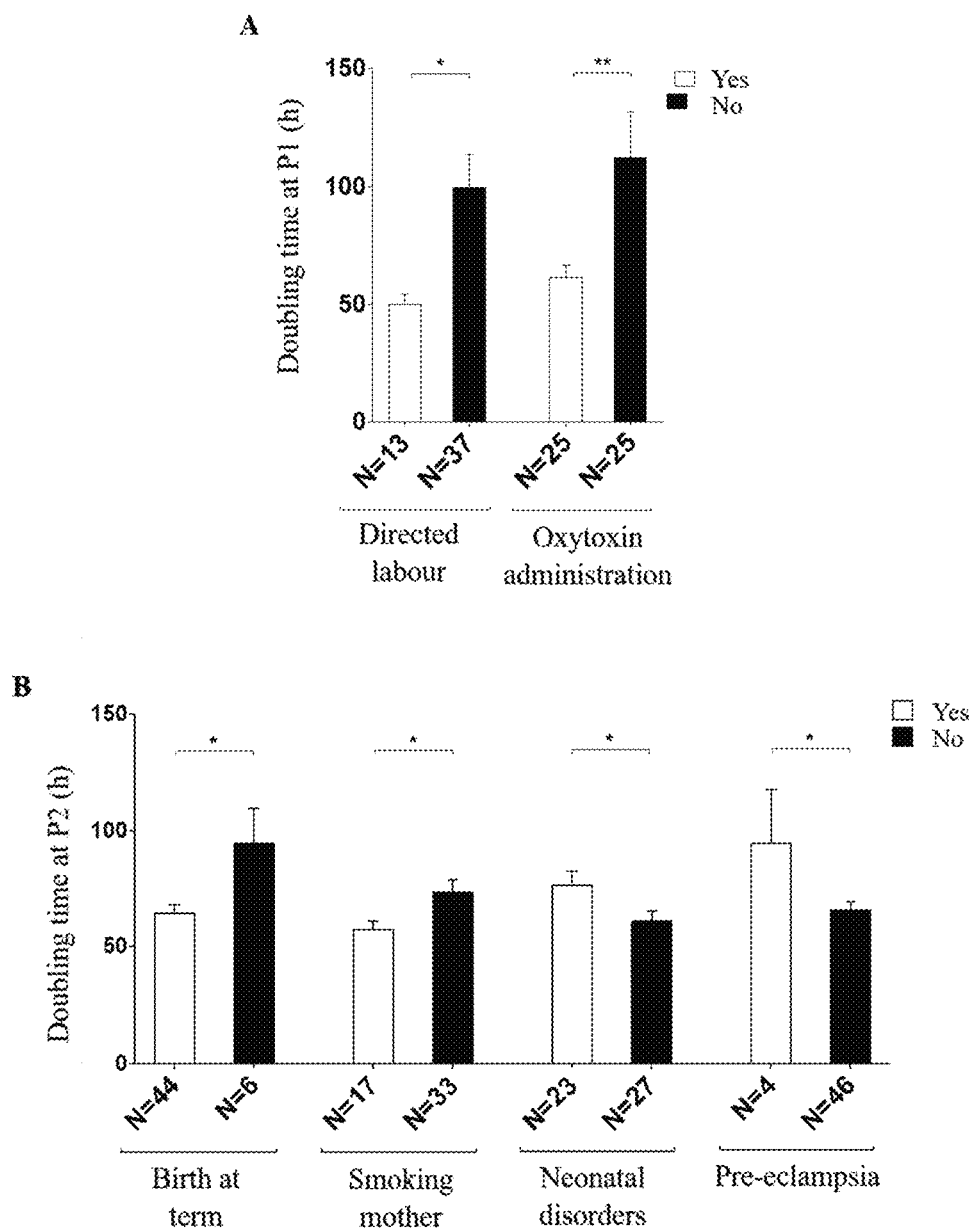
FIGS. 7A and B: these figures show the impact of obstetric factors on cell proliferation (A and B). The doubling time is inversely proportional to the proliferation. *: $p\leq0.05$ in bivariate regression, **: $p\leq0.05$ in multivariate regression.

According to a multivariate linear regression analysis, the administration of oxytocin at the time of labour showed a positive impact on the proliferation of WG-MSC by reducing the doubling time (61.6±5.2 hours vs. 112.0±19.5 hours, p=0.0159) during the first passage P1 (FIG. 7A). This administration of oxytocin also made it possible to obtain a larger number of cells with a short doubling time (<100 hours) (57.9% vs. 25%, p=0.0469). By considering only the samples with a doubling time in P1 below 100 hours, several factors showed a positive impact on the doubling time: directed labour (34.2% vs. 0%, p=0.0185), the number of weeks of amenorrhoea at birth (39.85 vs. 37.92, p=0.0212), maternal smoking (42.1% vs. 8.3%, p=0.0313) and the weight of the placenta (552.24 vs. 481.92, p=0.0446). At the second passage (P2), the weight at birth, the number of weeks of amenorrhoea, the weight of the placenta, a normal pregnancy and an absence of pre-eclampsia have shown a positive impact on cell proliferation (FIG. 7B). All these factors are linked to the concept of birth at term and make it possible to demonstrate that the WG-MSC, coming from newborns in good health and born at term, will present greater proliferative capacities. It is also observed that WG-MSC from umbilical cords of smoking mothers have increased proliferative capacities.

The identification of these factors promoting the proliferation of WG-MSC assists in the selection of umbilical cords which contain WG-MSC with the best proliferation properties.

BIBLIOGRAPHY

Alcayaga-Miranda, F., Cuenca, J., Martin, A., Contreras, L., Figueroa, F. E., and Khoury, M. (2015). Combination therapy of menstrual derived mesenchymal stem cells and antibiotics ameliorates survival in sepsis. Stem Cell Res. Ther. 6.

Chao, Y.-H., Wu, H.-P., Wu, K.-H., Tsai, Y.-G., Peng, C.-T., Lin, K.-C., Chao, W.-R., Lee, M.-S., and Fu, Y.-C. (2014a). An Increase in CD3+CD4+CD25+Regulatory T Cells after Administration of Umbilical Cord-Derived Mesenchymal Stem Cells during Sepsis. PLoS ONE 9, e110338.

Chinnadurai, R., Copland, I. B., Garcia, M. A., Petersen, C. T., Lewis, C. N., Waller, E. K., Kirk, A. D., and Galipeau, J. (2016). Cryopreserved Mesenchymal Stromal Cells Are Susceptible to T-Cell Mediated Apoptosis Which Is Partly Rescued by IFNγ Licensing. Stem Cells, 34(9), 2429-2442.

Condor, J. M., Rodrigues, C. E., Sousa Moreira, R. d., Canale, D., Volpini, R. A., Shimizu, M. H. M., Camara, N. O. S., Noronha, I. d. L., and Andrade, L. (2016). Treatment With Human Whartons Jelly-Derived Mesenchymal Stem Cells Attenuates Sepsis-Induced Kidney Injury, Liver Injury, and Endothelial Dysfunction. Stem Cells Transl. Med. 5, 1048-1057.

Devaney, J., Horie, S., Masterson, C., Elliman, S., Barry, F., O'Brien, T., Curley, G. F., O'Toole, D., and Laffey, J. G. (2015). Human mesenchymal stromal cells decrease the severity of acute lung injury induced by E. coli in the rat. Thorax 70, 625-635.

Dombrovskiy, V. Y., Martin, A. A., Sunderram, J., and Paz, H. L. (2007). Rapid increase in hospitalization and mortality rates for severe sepsis in the United States: A trend analysis from 1993 to 2003*: Crit. Care Med. 35, 1244-1250.

Francois M, Copland I B, Yuan S, Romieu-Mourez R, Waller E K, Galipeau J (2012). Cryopreserved mesenchymal stromal cells display impaired immunosuppressive properties as a result of heat-shock response and impaired interferon-γ licensing. Cytotherapy. 14(2):147-52.

Gonzalez-Rey, E., Anderson, P., Gonzalez, M. A., Rico, L., Büscher, D., and Delgado, M. (2009). Human adult stem cells derived from adipose tissue protect against experimental colitis and sepsis. Gut 58, 929-939.

Iskander, K. N., Osuchowski, M. F., Stearns-Kurosawa, D. J., Kurosawa, S., Stepien, D., Valentine, C., and Remick, D. G. (2013). Sepsis: Multiple Abnormalities, Heterogeneous Responses, and Evolving Understanding. Physiol. Rev. 93, 1247-1288.

Kim, H., Darwish, I., Monroy, M.-F., Prockop, D. J., Liles, W. C., and Kain, K. C. (2014). Mesenchymal stromal (stem) cells suppress pro-inflammatory cytokine production but fail to improve survival in experimental staphylococcal toxic shock syndrome. BMC Immunol. 15, 1.

Krasnodembskaya, A., Song, Y., Fang, X., Gupta, N., Serikov, V., Lee, J.-W., and Matthay, M. A. (2010). Antibacterial Effect of Human Mesenchymal Stem Cells Is Mediated in Part from Secretion of the Antimicrobial Peptide LL-37. STEM CELLS 28, 2229-2238.

Luo, C., Zhang, F., Zhang, L., Geng, Y., Li, Q., Hong, Q., Fu, B., Zhu, F., Cui, S., Feng, Z., et al. (2014). Mesenchymal Stem Cells Ameliorate Sepsis-associated Acute Kidney Injury in Mice: Shock 41, 123-129.

Mei, S. H., McCarter, S. D., Deng, Y., Parker, C. H., Liles, W. C., and Stewart, D. J. (2007). Prevention of LPS-induced acute lung injury in mice by mesenchymal stem cells overexpressing angiopoietin 1. PLoS Med. 4, e269.

Mezey, E., Nemeth K. (2015). Mesenchymal stem cells and infectious diseases: Smarter than drugs. Immunol. Lett. 168(2), 208-214.

Moll, G., Geilßler, S., Catar, R., Ignatowicz, L., Hoogduijn, M. J., Strunk, D., Bieback, K., and Ringdén, 0. (2016). Cryopreserved or Fresh Mesenchymal Stromal Cells: Only a Matter of Taste or Key to Unleash the Full Clinical Potential of MSC Therapy? In F. Karimi-Busheri & M. Weinfeld (Eds.), Biobanking and cryopreservation of stem cells. (Vol. 951, Advances in Experimental Medicine and Biology., pp. 77-98). Cham, Switzerland: Springer.

Németh, K., Leelahavanichkul, A., Yuen, P. S. T., Mayer, B., Parmelee, A., Doi, K., Robey, P. G., Leelahavanichkul, K., Koller, B. H., Brown, J. M., et al. (2009). Bone marrow stromal cells attenuate sepsis via prostaglandin E2-dependent reprogramming of host macrophages to increase their interleukin-10 production. Nat. Med. 15, 42-49.

Pedrazza, L., Lunardelli, A., Luft, C., Cruz, C. U., de Mesquita, F. C., Bitencourt, S., Nunes, F. B., and de Oliveira, J. R. (2014). Mesenchymal stem cells decrease splenocytes apoptosis in a sepsis experimental model. Inflamm. Res. 63, 719-728.

Rojas, M., Cárdenes, N., Kocyildirim, E., Tedrow, J. R., Cáceres, E., Deans, R., Ting, A., and Bermúdez, C. (2014). Human adult bone marrow-derived stem cells decrease severity of lipopolysaccharide-induced acute respiratory distress syndrome in sheep. Stem Cell Res. Ther. 5, 42.

Wu, K.-H., Wu, H.-P., Chao, W.-R., Lo, W.-Y., Tseng, P.-C., Lee, C.-J., Peng, C.-T., Lee, M.-S., and Chao, Y.-H. (2015). Time-Series Expression of Toll-Like Receptor 4 Signaling in Septic Mice Treated with Mesenchymal Stem Cells: SHOCK 1.

Zhao, X., Liu, D., Gong, W., Zhao, G., Liu, L., Yang, L., and Hou, Y. (2014). The Toll-like Receptor 3 Ligand, Poly(I: C), Improves Immunosuppressive Function and Therapeutic Effect of Mesenchymal Stem Cells on Sepsis via Inhibiting MiR-143: Poly(I:C) Improves MSCs Immune Function. STEM CELLS 32, 521-533.

Mervyn Singer, Clifford S. Deutschman, Christopher Warren Seymour, Manu Shankar-Hari, Djillali Annane, Michael Bauer, Rinaldo Bellomo, Gordon R. Bernard, Jean-Daniel Chiche, Craig M. Coopersmith, Richard S. Hotchkiss, Mitchell M. Levy, John C. Marshall, Greg S.

Martin, Steven M. Opal, Gordon D. Rubenfeld, Tom van der Poll, Jean-Louis Vincent, and Derek C. Angus. (2016). The Third International Consensus Definitions for Sepsis and Septic Shock (Sepsis-3). JAMA. 2016; 315(8):801-810

The invention claimed is:

1. A method of treating septic shock in a subject in need thereof, comprising administering to said subject thawed human mesenchymal stem cells (MSC) from Wharton's jelly, which were previously cryopreserved at a temperature between a range from −150° C. and −196° C. in a cryoprotectant solution containing at least one cryoprotectant prior to being thawed, said at least one cryoprotectant being selected from the group consisting of dimethyl sulfoxide, glycerol, ethylene glycol, propylene glycol, formamide, butene diol, and combinations thereof,
  wherein the expression level of the marker CD44 is at least 10% lower in said thawed human MSC from Wharton's jelly than the expression level of the marker CD44 in fresh human MSC from Wharton's jelly,
  wherein said thawed human MSC from Wharton's jelly secrete at least 1.5 times more TGFβ3 than fresh human MSC from Wharton's jelly, and
  wherein at least 80% of said thawed human MSC from Wharton's jelly do not express CD34.

2. The method according to claim 1, wherein the expression level of at least one marker selected from CD90, CD73, CD105, CD29, CD146, CD166, HLA-ABC is at least 10% lower in said thawed human MSC from Wharton's jelly than the expression level of the same marker in fresh human MSC from Wharton's jelly.

3. The method according to claim 1, wherein the expression level of the marker CD90 is at least 10% lower in said thawed human MSC from Wharton's jelly than the expression level of the marker CD90 in fresh human MSC from Wharton's jelly.

4. The method according to claim 1, wherein said thawed human MSC from Wharton's jelly express at least one protein selected from the group comprising ACTB, ANXA1, CAPZB, LASP1, PRDX2, PRDX3, PSA3, RS12 and SYWC.

5. The method according to claim 1, wherein said thawed human MSC from Wharton's jelly do not express at least one protein selected from the group comprising ACTS, AL1B1, ANX10, GBB1, GBB2, GPRIN1, DTNA, MIPO1, PSB3 and PSDE.

6. The method according to claim 1, wherein said thawed human MSC from Wharton's jelly, in in vitro condition and/or in non-inflammatory condition, further secrete at least one growth factor selected from BMP-7, IGFBP-1, insulin, FGF-7, NT-4 and VEGF-D.

7. The method according to claim 1, wherein said thawed human MSC from Wharton's jelly, in in vivo condition and/or in non-inflammatory condition, further secrete BMP-7.

8. The method according to claim 1, wherein said thawed human MSC from Wharton's jelly, in in vivo condition and/or in inflammatory condition, do not secrete IGFBP-1.

9. The method according to claim 1, wherein said thawed human MSC from Wharton's jelly secrete at least 1.2 times more VEGF than fresh human MSC from Wharton's jelly.

10. The method according to claim 1, wherein said thawed human MSC from Wharton's jelly induce an increase in the VEGF serum concentration in patients, by at least 5% with respect to fresh human MSC from Wharton's jelly.

11. The method according to claim 1, wherein said thawed human MSC from Wharton's jelly are from the human umbilical cord tissue coming from a mother meeting at least one of the following criteria: having received an administration of oxytocin during childbirth, having given birth by directed labour, having given birth at term, not having presented pre-eclampsia during the pregnancy, whose child has not presented neonatal disorders and having been subject to an intake of tobacco smoke during the pregnancy.

12. The method according to claim 1, wherein said thawed human MSC from Wharton's jelly are clinical grade cells.

13. The method according to claim 1, wherein said thawed human MSC from Wharton's jelly are obtained directly from thawing without reculturing after thawing.

14. The method according to claim 1 wherein the subject in need thereof is being treated with at least one vasopressor agent.

15. The method according to claim 14, wherein the at least one vasopressor agent is selected from the group consisting of catecholamines and vasopressin.

16. A method of treating septic shock in a subject in need thereof, comprising administering to said subject a pharmaceutical composition comprising thawed human mesenchymal stem cells (MSC) from Wharton's jelly and a pharmaceutically acceptable excipient,
  wherein the pharmaceutical composition was previously cryopreserved at a temperature between a range from −150° C. and −196° C. in a cryoprotectant solution containing at least one cryoprotectant prior to being thawed, said at least one cryoprotectant being selected from the group consisting of dimethyl sulfoxide, glycerol, ethylene glycol, propylene glycol, formamide, butene diol, and combinations thereof,
  wherein the expression level of the marker CD44 is at least 10% lower in said thawed human MSC from Wharton's jelly than the expression level of the marker CD44 in fresh human MSC from Wharton's jelly,
  wherein said thawed human MSC from Wharton's jelly secrete at least 1.5 times more TGFβ3 than fresh human MSC from Wharton's jelly, and
  wherein at least 80% of said thawed human MSC from Wharton's jelly do not express CD34.

17. The method according to claim 16 wherein the subject in need thereof is being treated with at least one vasopressor agent.

* * * * *